United States Patent
Baker-Glenn et al.

(10) Patent No.: US 9,212,173 B2
(45) Date of Patent: *Dec. 15, 2015

(54) PYRAZOLE AMINOPYRIMIDINE DERIVATIVES AS LRRK2 MODULATORS

(71) Applicant: Genentech, Inc., South San Francisco, CA (US)

(72) Inventors: Charles Baker-Glenn, St. Neots (GB); Daniel Jon Burdick, Burlingame, CA (US); Bryan K. Chan, San Carlos, CA (US); Mark Chambers, Puckeridge (GB); Huifen Chen, Burlingame, CA (US); Anthony Estrada, San Carlos, CA (US); Zachary Kevin Sweeney, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/531,271

(22) Filed: Nov. 3, 2014

(65) Prior Publication Data

US 2015/0051238 A1     Feb. 19, 2015

Related U.S. Application Data

(63) Continuation of application No. PCT/EP2013/058939, filed on Apr. 30, 2013.

(60) Provisional application No. 61/642,019, filed on May 3, 2012.

(51) Int. Cl.
| | |
|---|---|
| *A61K 31/506* | (2006.01) |
| *C07D 403/12* | (2006.01) |
| *C07D 413/14* | (2006.01) |
| *C07D 403/14* | (2006.01) |
| *C07D 407/14* | (2006.01) |
| *C07D 405/14* | (2006.01) |

(52) U.S. Cl.
CPC ............ *C07D 403/12* (2013.01); *C07D 403/14* (2013.01); *C07D 405/14* (2013.01); *C07D 407/14* (2013.01); *C07D 413/14* (2013.01); *A61K 31/506* (2013.01)

(58) Field of Classification Search
CPC .. C07D 403/12; C07D 403/14; C07D 405/14; C07D 407/14; C07D 413/14; A61K 31/506
USPC .......................................... 544/295; 514/275
See application file for complete search history.

(56) References Cited

U.S. PATENT DOCUMENTS

| | | | |
|---|---|---|---|
| 8,637,537 B2 * | 1/2014 | Aliagas-Martin et al. | 514/275 |
| 8,669,251 B2 * | 3/2014 | Crawford et al. | 514/230.5 |
| 8,697,715 B2 * | 4/2014 | Blake et al. | 514/274 |
| 8,815,882 B2 * | 8/2014 | Baker-Glenn et al. | 514/272 |
| 2011/0224197 A1 * | 9/2011 | Henkel et al. | 514/228.2 |
| 2012/0157427 A1 * | 6/2012 | Baker-Glenn et al. | 514/210.2 |
| 2013/0116246 A1 * | 5/2013 | Crawford et al. | 514/230.5 |
| 2013/0225620 A1 * | 8/2013 | Aliagas-Martin et al. | 514/275 |
| 2013/0252934 A1 * | 9/2013 | Blake et al. | 514/210.2 |
| 2013/0281432 A1 * | 10/2013 | Currie et al. | 514/210.21 |
| 2014/0088117 A1 * | 3/2014 | Burch et al. | 514/255.05 |
| 2014/0128401 A1 * | 5/2014 | Crawford et al. | 514/248 |
| 2014/0249127 A1 * | 9/2014 | Blake et al. | 514/210.2 |
| 2014/0328805 A1 * | 11/2014 | Estrada et al. | 424/93.7 |

FOREIGN PATENT DOCUMENTS

| | | | |
|---|---|---|---|
| WO | WO 2006074057 A2 * | 7/2006 | |
| WO | WO 2012062783 A1 * | 5/2012 | |

\* cited by examiner

*Primary Examiner* — Alexander R Pagano
(74) *Attorney, Agent, or Firm* — Robert C. Hall

(57) ABSTRACT

Pyrazole compounds that are modulators of LRRK2, methods of making the compounds, and methods for using the compounds for treatment of diseases associated with LRRK2 receptor, such as Parkinson's disease.

3 Claims, No Drawings

PYRAZOLE AMINOPYRIMIDINE DERIVATIVES AS LRRK2 MODULATORS

CROSS REFERENCE TO RELATED APPLICATIONS

This application is a continuation of PCT/EP2013/058939 filed on Apr. 30, 2013, which claims priority to U.S. Provisional Application No. 61/642,019 filed May 3, 2012, the disclosures of which are incorporated herein by reference in their entirety.

FIELD OF THE INVENTION

This invention pertains to compounds that modulate the function of LRRK2 and are useful for treatment of LRRK2-mediated diseases and conditions such as Parkinson's disease.

BACKGROUND OF THE INVENTION

Neurodegenerative diseases such as Parkinson's disease, Lewy body dementia and Huntington's disease affect millions of individuals. Parkinson's disease is a chronic, progressive motor system disorder that afflicts approximately one out of every 1000 people, with hereditary Parkinson's disease accounting for 5-10% of all of patients. Parkinson's disease is caused by progressive loss of mid-brain dopamine neurons, leaving patients with impaired ability to direct and control their movements. The primary Parkinson's disease symptoms are trembling, rigidity, slowness of movement, and impaired balance. Many Parkinson's disease patients also experience other symptoms such as emotional changes, memory loss, speech problems, and sleeping disorders.

The gene encoding the leucine-rich repeat kinase 2 protein (LRRK2) has been identified in association with hereditary Parkinson's disease (Paisan-Ruiz et al., *Neuron*, Vol. 44(4), 2004, pp 595-600; Zimprich et al., *Neuron*, Vol. 44(4), 2004, 601-607). In-vitro studies show that Parkinson's disease-associated mutation leads to increased LRRK2 kinase activity and decreased rate of GTP hydrolysis compared to wild-type (Guo et al., *Experimental Cell Research*, Vol. 313(16), 2007, pp. 3658-3670. Anti-LRRK2 antibodies have been used to label brainstem Lewy bodies associated with Parkinson's disease and cortical antibodies associated with Lewis body dementia suggesting that LRRK2 may play an important role in Lewie body formation and pathogenesis associated with these diseases (Zhou et al., *Molecular Degeneration,* 2006, 1:17 doi:10.1186/1750-1326-1-17). LRRK2 has also been identified as a gene potentially associated with increased susceptibility to Crohn's disease and susceptibility to leprosy (Zhang et al., *New England J. Med.* Vol. 361 (2009) pp. 2609-2618.

LRRK2 has also been associated with the transition of mild cognitive impairment to Alzheimer's disease (WO2007/149789); L-Dopa induced dyskinesia (Hurley et al., *Eur. J. Neurosci.*, Vol. 26, 2007, pp. 171-177; CNS disorders associated with neuronal progenitor differentiation (Milosevic et al., *Neurodegen.*, Vol. 4, 2009, p. 25); cancers such as kidney, breast, prostate, blood and lung cancers and acute myelogenous leukemia (WO2011/038572); papillary renal and thyroid carcinomas (Looyenga et al., www.pnas.org/cgi/doi/10.1073/pnas.1012500108); multiple myeloma (Chapman et al., *Nature* Vol. 471, 2011, pp. 467-472); amyotrophic lateral sclerosis (Shtilbans et al., *Amyotrophic Lateral Sclerosis* "Early Online 2011, pp. 1-7); rheumatoid arthritis (Nakamura et al., *DNA Res.* Vol. 13(4), 2006, pp. 169-183); and ankylosing spondylytis (Danoy et al., *PLoS Genetics*, Vol. 6(12), 2010, e1001195, pp. 1-5).

Accordingly, compounds and compositions effective at modulating LRRK2 activity may provide a treatment for neurodegenerative diseases such as Parkinson's disease and Lewie body dementia, for CNS disorders such as Alzheimer's disease and L-Dopa induced dyskinesia, for cancers such as kidney, breast, prostate, blood, papillary and lung cancers, acute myelogenous leukemia and multiple myeloma, and for inflammatory diseases such as leprosy, Crohn's disease, amyotrophic lateral sclerosis, rheumatoid arthritis, and ankylosing spondylytis. Particularly, there is a need for compounds with LRRK2 affinity that are selective for LRRK2 over other kinases, such as JAK2, which can provide effective drugs for treatment of neurodegenerative disorders such as PD.

SUMMARY OF THE INVENTION

The invention provides compounds selected from:
$N^2$-(1',5-dimethyl-1'H-1,4'-bipyrazol-4-yl)-N4-methyl-5-(trifluoromethyl)pyrimidine-2,4-diamine;
$N^2$-(1',3-dimethyl-1'H-1,4'-bipyrazol-4-yl)-N4-methyl-5-(trifluoromethyl)pyrimidine-2,4-diamine;
4-(cyclopropylamino)-2-((5-methyl-1-(tetrahydro-2H-pyran-4-yl)-1H-pyrazol-4-yl)amino)pyrimidine-5-carbonitrile;
4-(cyclopropylamino)-2-((3-methyl-1-(tetrahydro-2H-pyran-4-yl)-1H-pyrazol-4-yl)amino)pyrimidine-5-carbonitrile;
2-((1-(1-cyanopropyl)-5-methyl-1H-pyrazol-4-yl)amino)-4-(cyclopropylamino)pyrimidine-5-carbonitrile;
N2-(1-(1-fluoro-2-methylpropan-2-yl)-3-methyl-1H-pyrazol-4-yl)-N4-methyl-5-(trifluoromethyl)pyrimidine-2,4-diamine;
2-((5-chloro-1-(tetrahydro-2H-pyran-4-yl)-1H-pyrazol-4-yl)amino)-4-(ethylamino)pyrimidine-5-carbonitrile;
5-bromo-$N^2$-(1,5-dimethyl-1H-pyrazol-4-yl)-$N^4$-methylpyrimidine-2,4-diamine;
2-methyl-2-(3-methyl-4-((4-(methylamino)-5-(trifluoromethyl)pyrimidin-2-yl)amino)-1H-pyrazol-1-yl)propan-1-ol;
1-((5-chloro-4-((4-(methylamino)-5-(trifluoromethyl)pyrimidin-2-yl)amino)-1H-pyrazol-1-yl)methyl)cyclopropanol;
N2-(3-chloro-1-(2-(4-ethyl-4H-1,2,4-triazol-3-yl)propan-2-yl)-1H-pyrazol-4-yl)-N4-methyl-5-(trifluoromethyl)pyrimidine-2,4-diamine;
N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;
N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;
N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;
N4-methyl-N2-(3-methyl-1-(3-methyloxetan-3-yl)-1H-pyrazol-4-yl)-5-(trifluoromethyl)pyrimidine-2,4-diamine;
N2-(1-(2-(1,4-dimethyl-1H-imidazol-2-yl)propan-2-yl)-3-methyl-1H-pyrazol-4-yl)-N4-methyl-5-(trifluoromethyl)pyrimidine-2,4-diamine;
N2-(1-(2-(1,4-dimethyl-1H-imidazol-2-yl)propan-2-yl)-3-methyl-1H-pyrazol-4-yl)-N4-methyl-5-(trifluoromethyl)pyrimidine-2,4-diamine;

N4-methyl-N2-(3-methyl-1-(2-(5-methyloxazol-2-yl)propan-2-yl)-1H-pyrazol-4-yl)-5-(trifluoromethyl)pyrimidine-2,4-diamine;

N4-ethyl-N2-(3-methyl-1-(3-methyloxetan-3-yl)-1H-pyrazol-4-yl)-5-(trifluoromethyl)pyrimidine-2,4-diamine;

N4-ethyl-N2-(1-((2-methoxyethyl)sulfonyl)-3-methyl-1H-pyrazol-4-yl)-5-(trifluoromethyl)pyrimidine-2,4-diamine;

N2-(1-((2-methoxyethyl)sulfonyl)-3-methyl-1H-pyrazol-4-yl)-N4-methyl-5-(trifluoromethyl)pyrimidine-2,4-diamine;

N2-(1-((2-methoxyethyl)sulfonyl)-5-methyl-1H-pyrazol-4-yl)-N4-methyl-5-(trifluoromethyl)pyrimidine-2,4-diamine;

N2-(5-chloro-1-(2-(4-methyl-4H-1,2,4-triazol-3-yl)propan-2-yl)-1H-pyrazol-4-yl)-N4-ethyl-5-(trifluoromethyl)pyrimidine-2,4-diamine;

N4-methyl-N2-(5-methyl-1-(2-(1-methyl-1H-pyrazol-3-yl)propyl)-1H-pyrazol-4-yl)-5-(trifluoromethyl)pyrimidine-2,4-diamine;

N4-methyl-N2-(5-methyl-1-(2-(1-methyl-1H-pyrazol-3-yl)propyl)-1H-pyrazol-4-yl)-5-(trifluoromethyl)pyrimidine-2,4-diamine;

N4-methyl-N2-(3-methyl-1-(2-(pyrimidin-2-yl)propan-2-yl)-1H-pyrazol-4-yl)-5-(trifluoromethyl)pyrimidine-2,4-diamine;

N2-(3-chloro-1-(2-(5-methyl-1,3,4-oxadiazol-2-yl)propan-2-yl)-1H-pyrazol-4-yl)-N4-ethyl-5-(trifluoromethyl)pyrimidine-2,4-diamine;

$N^4$-ethyl-$N^2$-(3-methyl-1-(2-(5-methyl-1,3,4-oxadiazol-2-yl)propan-2-yl)-1H-pyrazol-4-yl)-5-(trifluoromethyl)pyrimidine-2,4-diamine;

N4-ethyl-N2-(1-(2-(5-ethyl-1,3,4-oxadiazol-2-yl)propan-2-yl)-3-methyl-1H-pyrazol-4-yl)-5-(trifluoromethyl)pyrimidine-2,4-diamine;

N4-ethyl-N2-(1-(2-(1-isopropyl-1H-1,2,4-triazol-3-yl)propan-2-yl)-3-methyl-1H-pyrazol-4-yl)-5-(trifluoromethyl)pyrimidine-2,4-diamine;

N2-(3-chloro-1-(2-(4-methyl-4H-1,2,4-triazol-3-yl)propan-2-yl)-1H-pyrazol-4-yl)-N4-ethyl-5-(trifluoromethyl)pyrimidine-2,4-diamine;

N2-(3-chloro-1-(2-(1-methyl-1H-1,2,4-triazol-3-yl)propan-2-yl)-1H-pyrazol-4-yl)-N4-ethyl-5-(trifluoromethyl)pyrimidine-2,4-diamine;

N4-methyl-N2-(5-methyl-1-(2-(1-methyl-1H-pyrazol-3-yl)ethyl)-1H-pyrazol-4-yl)-5-(trifluoromethyl)pyrimidine-2,4-diamine;

N4-ethyl-N2-(3-methyl-1-(2-(1-methyl-1H-pyrazol-3-yl)propan-2-yl)-1H-pyrazol-4-yl)-5-(trifluoromethyl)pyrimidine-2,4-diamine;

N4-ethyl-N2-(3-methyl-1-(2-(1-methyl-1H-pyrazol-5-yl)propan-2-yl)-1H-pyrazol-4-yl)-5-(trifluoromethyl)pyrimidine-2,4-diamine;

N4-methyl-N2-(3-methyl-1-(2-(1-methyl-1H-pyrazol-3-yl)ethyl)-1H-pyrazol-4-yl)-5-(trifluoromethyl)pyrimidine-2,4-diamine;

N2-(1-(3-fluorotetrahydro-2H-pyran-4-yl)-3-methyl-1H-pyrazol-4-yl)-N4-methyl-5-(trifluoromethyl)pyrimidine-2,4-diamine;

N2-(1-(3-fluorotetrahydro-2H-pyran-4-yl)-3-methyl-1H-pyrazol-4-yl)-N4-methyl-5-(trifluoromethyl)pyrimidine-2,4-diamine;

N2-(1-(3-fluorotetrahydro-2H-pyran-4-yl)-5-methyl-1H-pyrazol-4-yl)-N4-methyl-5-(trifluoromethyl)pyrimidine-2,4-diamine;

N2-(1-((3R)-3-fluorotetrahydro-2H-pyran-4-yl)-5-methyl-1H-pyrazol-4-yl)-N4-methyl-5-(trifluoromethyl)pyrimidine-2,4-diamine 3-methyl-3-(3-methyl-4-((4-(methylamino)-5-(trifluoromethyl)pyrimidin-2-yl)amino)-1H-pyrazol-1-yl)butanenitrile;

2-((3-methyl-4-((4-(methylamino)-5-(trifluoromethyl)pyrimidin-2-yl)amino)-1H-pyrazol-1-yl)methyl)butanenitrile;

3-methyl-3-(3-methyl-4-((4-(methylamino)-5-(trifluoromethyl)pyrimidin-2-ylamino)-1H-pyrazol-1-yl)butanenitrile;

2-(5-((4-(ethylamino)-5-(trifluoromethyl)pyrimidin-2-yl)amino)-1-methyl-1H-pyrazol-3-yl)-2-methylpropanenitrile;

2-methyl-2-(1-methyl-5-((4-(methylamino)-5-(trifluoromethyl)pyrimidin-2-yl)amino)-1H-pyrazol-3-yl)propanenitrile;

2-((1-(2-cyanopropan-2-yl)-3-methyl-1H-pyrazol-4-yl)amino)-4-(cyclopropylamino)pyrimidine-5-carbonitrile;

2-((1-(2-cyanopropan-2-yl)-3-methyl-1H-pyrazol-4-yl)amino)-4-(cyclopropylamino)pyrimidine-5-carbonitrile;

2-((1-(2-cyanopropan-2-yl)-3-methyl-1H-pyrazol-4-yl)amino)-4-(ethylamino)pyrimidine-5-carbonitrile;

2-methyl-2-(3-methyl-4-((4-(methylamino)-5-(trifluoromethyl)pyrimidin-2-yl)amino)-1H-pyrazol-1-yl)butanenitrile; and 5-((4-(ethylamino)-5-(trifluoromethyl)pyrimidin-2-yl)amino)-1-methyl-1H-pyrazole-3-carbonitrile, or a pharmaceutical salt thereof.

The invention also provides pharmaceutical compositions comprising the compounds, methods of using the compounds, and methods of preparing the compounds.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy' means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —SO$_2$—R, wherein R is alkyl as defined herein.

"Alkylsulfonylalkyl means a moiety of the formula —R'—SO$_2$—R" where R' is alkylene and R" is alkyl as defined herein.

"Alkylsulfonylalkoxy" means a group of the formula —O—R—SO$_2$—R' wherein R is alkylene and R' is alkyl as defined herein.

"Amino means a moiety of the formula —NRR' wherein R and R' each independently is hydrogen or alkyl as defined herein. "Amino thus includes "alkylamino" (where one of R and R' is alkyl and the other is hydrogen) and "dialkylamino" (where R and R' are both alkyl.

"Aminocarbonyl" means a group of the formula —C(O)—R wherein R is amino as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO$_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —SO$_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl"" means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Heteroalkyl" means an alkyl radical as defined herein wherein one, two or three hydrogen atoms have been replaced with a substituent independently selected from the group consisting of –OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, amino sulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each optionally substituted.

"Heteroarylalkyl" or "heteroaralkyl" means a group of the formula —R—R' wherein R is alkylene and R' is heteroaryl as defined herein.

"Heteroarylsulfonyl" means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Alkoxy hydroxyalkyl" and "hydroxy alkoxyalkyl", which may be used interchangeably, means an alkyl as defined herein that is substituted at least once with hydroxy and at least once with alkoxy. "Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted", when used in association with "aryl", phenyl", "heteroaryl" "cycloalkyl" or "heterocyclyl", means an aryl, phenyl, heteroaryl, cycloalkyl or heterocyclyl which is optionally substituted independently with one to four substituents, for example one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR, —SO$_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). Certain particular optional substituents for "aryl", phenyl", "heteroaryl" "cycloalkyl" or "heterocyclyl" include alkyl, halo, haloalkyl, alkoxy, cyano, amino and alkylsulfonyl. In one embodiment substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Parkinson's disease" means a degenerative disorder of the central nervous system that impairs motor skills, speech, and/or cognitive function. Symptoms of Parkinson's disease may include, for example, muscle rigidity, tremor, slowing of physical movement (bradykinesia) and loss of physical movement (akinesia).

"Lewie (Lewy) body disease" also called "Lewie body dementia", diffuse Lewie body disease", cortical Lewie body disease", means a neurodegenerative disorder characterized anatomically by the presence of Lewie bodies in the brain.

"Subject" means mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where one or more chiral centers exist in a structure but no specific stereochemistry is shown for the chiral centers, both enantiomers associated with each such chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes.

All patents and publications identified herein are incorporated herein by reference in their entirety.

Compounds of the Invention

A certain embodiment of the invention relates to a compound of the formula I:

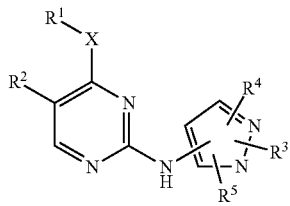

or a pharmaceutically acceptable salt thereof,
wherein:
X is: —NH;
$R^1$ is: $C_{1-6}$alkyl or $C_{3-6}$cycloalkyl;
$R^2$ is: halo; cyano or halo-$C_{1-6}$alkyl;
$R^3$ is: hydrogen; $C_{1-6}$alkyl; halo-$C_{1-6}$alkyl; hydroxy-$C_{1-6}$alkyl; cyano-$C_{1-6}$alkyl; $C_{1-6}$alkoxysulfonyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; heterocyclyl optionally substituted one or more times with $R^7$; heterocyclyl-$C_{1-6}$alkyl wherein the heterocyclyl portion is optionally substituted one or more times with $R^7$; heteroaryl optionally substituted one or more times with $R^8$; or heteroaryl-$C_{1-6}$alkyl wherein the heteroaryl portion is optionally substituted one or more times with $R^8$;
$R^4$ is: hydrogen; $C_{1-6}$alkyl; or halo;
$R^5$ is: hydrogen; or $C_{1-6}$alkyl;
each $R^6$ is independently: $C_{1-6}$alkyl or hydroxy;
each $R^7$ is independently: $C_{1-6}$alkyl; or halo; and
each $R^8$ is independently: $C_{1-6}$alkyl or halo-$C_{1-6}$alkyl;
wherein the compound is selected from
N²-(1',5-dimethyl-1'H-1,4'-bipyrazol-4-yl)-N4-methyl-5-(trifluoromethyl)pyrimidine-2,4-diamine;
N²-(1',3-dimethyl-1'H-1,4'-bipyrazol-4-yl)-N4-methyl-5-(trifluoromethyl)pyrimidine-2,4-diamine;
4-(cyclopropylamino)-2-((5-methyl-1-(tetrahydro-2H-pyran-4-yl)-1H-pyrazol-4-yl)amino)pyrimidine-5-carbonitrile;
4-(cyclopropylamino)-2-((3-methyl-1-(tetrahydro-2H-pyran-4-yl)-1H-pyrazol-4-yl)amino)pyrimidine-5-carbonitrile;
2-((1-(1-cyanopropyl)-5-methyl-1H-pyrazol-4-yl)amino)-4-(cyclopropylamino)pyrimidine-5-carbonitrile;
N2-(1-(1-fluoro-2-methylpropan-2-yl)-3-methyl-1H-pyrazol-4-yl)-N4-methyl-5-(trifluoromethyl)pyrimidine-2,4-diamine;
2-((5-chloro-1-(tetrahydro-2H-pyran-4-yl)-1H-pyrazol-4-yl)amino)-4-(ethylamino)pyrimidine-5-carbonitrile;
5-bromo-N²-(1,5-dimethyl-1H-pyrazol-4-yl)-N⁴-methylpyrimidine-2,4-diamine;
2-methyl-2-(3-methyl-4-((4-(methylamino)-5-(trifluoromethyl)pyrimidin-2-yl)amino)-1H-pyrazol-1-yl)propan-1-ol;
1-((5-chloro-4-((4-(methylamino)-5-(trifluoromethyl)pyrimidin-2-yl)amino)-1H-pyrazol-1-yl)methyl)cyclopropanol;
N2-(3-chloro-1-(2-(4-ethyl-4H-1,2,4-triazol-3-yl)propan-2-yl)-1H-pyrazol-4-yl)-N4-methyl-5-(trifluoromethyl)pyrimidine-2,4-diamine;
N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;
N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;
N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;
N4-methyl-N2-(3-methyl-1-(3-methyloxetan-3-yl)-1H-pyrazol-4-yl)-5-(trifluoromethyl)pyrimidine-2,4-diamine;
N2-(1-(2-(1,4-dimethyl-1H-imidazol-2-yl)propan-2-yl)-3-methyl-1H-pyrazol-4-yl)-N4-methyl-5-(trifluoromethyl)pyrimidine-2,4-diamine;
N2-(1-(2-(1,4-dimethyl-1H-imidazol-2-yl)propan-2-yl)-3-methyl-1H-pyrazol-4-yl)-N4-methyl-5-(trifluoromethyl)pyrimidine-2,4-diamine;
N4-methyl-N2-(3-methyl-1-(2-(5-methyloxazol-2-yl)propan-2-yl)-1H-pyrazol-4-yl)-5-(trifluoromethyl)pyrimidine-2,4-diamine;
N4-ethyl-N2-(3-methyl-1-(3-methyloxetan-3-yl)-1H-pyrazol-4-yl)-5-(trifluoromethyl)pyrimidine-2,4-diamine;
N4-ethyl-N2-(1-((2-methoxyethyl)sulfonyl)-3-methyl-1H-pyrazol-4-yl)-5-(trifluoromethyl)pyrimidine-2,4-diamine;
N2-(1-((2-methoxyethyl)sulfonyl)-3-methyl-1H-pyrazol-4-yl)-N4-methyl-5-(trifluoromethyl)pyrimidine-2,4-diamine;
N2-(1-((2-methoxyethyl)sulfonyl)-5-methyl-1H-pyrazol-4-yl)-N4-methyl-5-(trifluoromethyl)pyrimidine-2,4-diamine;
N2-(5-chloro-1-(2-(4-methyl-4H-1,2,4-triazol-3-yl)propan-2-yl)-1H-pyrazol-4-yl)-N4-ethyl-5-(trifluoromethyl)pyrimidine-2,4-diamine;
N4-methyl-N2-(5-methyl-1-(2-(1-methyl-1H-pyrazol-3-yl)propyl)-1H-pyrazol-4-yl)-5-(trifluoromethyl)pyrimidine-2,4-diamine;
N4-methyl-N2-(5-methyl-1-(2-(1-methyl-1H-pyrazol-3-yl)propyl)-1H-pyrazol-4-yl)-5-(trifluoromethyl)pyrimidine-2,4-diamine;

N4-methyl-N2-(3-methyl-1-(2-(pyrimidin-2-yl)propan-2-yl)-1H-pyrazol-4-yl)-5-(trifluoromethyl)pyrimidine-2,4-diamine;

N2-(3-chloro-1-(2-(5-methyl-1,3,4-oxadiazol-2-yl)propan-2-yl)-1H-pyrazol-4-yl)-N4-ethyl-5-(trifluoromethyl)pyrimidine-2,4-diamine;

N4-ethyl-N2-(3-methyl-1-(2-(5-methyl-1,3,4-oxadiazol-2-yl)propan-2-yl)-1H-pyrazol-4-yl)-5-(trifluoromethyl)pyrimidine-2,4-diamine;

N4-ethyl-N2-(1-(2-(5-ethyl-1,3,4-oxadiazol-2-yl)propan-2-yl)-3-methyl-1H-pyrazol-4-yl)-5-(trifluoromethyl)pyrimidine-2,4-diamine;

N4-ethyl-N2-(1-(2-(1-isopropyl-1H-1,2,4-triazol-3-yl)propan-2-yl)-3-methyl-1H-pyrazol-4-yl)-5-(trifluoromethyl)pyrimidine-2,4-diamine;

N2-(3-chloro-1-(2-(4-methyl-4H-1,2,4-triazol-3-yl)propan-2-yl)-1H-pyrazol-4-yl)-N4-ethyl-5-(trifluoromethyl)pyrimidine-2,4-diamine;

N2-(3-chloro-1-(2-(1-methyl-1H-1,2,4-triazol-3-yl)propan-2-yl)-1H-pyrazol-4-yl)-N4-ethyl-5-(trifluoromethyl)pyrimidine-2,4-diamine;

N4-methyl-N2-(5-methyl-1-(2-(1-methyl-1H-pyrazol-3-yl)ethyl)-1H-pyrazol-4-yl)-5-(trifluoromethyl)pyrimidine-2,4-diamine;

N4-ethyl-N2-(3-methyl-1-(2-(1-methyl-1H-pyrazol-3-yl)propan-2-yl)-1H-pyrazol-4-yl)-5-(trifluoromethyl)pyrimidine-2,4-diamine;

N4-ethyl-N2-(3-methyl-1-(2-(1-methyl-1H-pyrazol-5-yl)propan-2-yl)-1H-pyrazol-4-yl)-5-(trifluoromethyl)pyrimidine-2,4-diamine;

N4-methyl-N2-(3-methyl-1-(2-(1-methyl-1H-pyrazol-3-yl)ethyl)-1H-pyrazol-4-yl)-5-(trifluoromethyl)pyrimidine-2,4-diamine;

N2-(1-(3-fluorotetrahydro-2H-pyran-4-yl)-3-methyl-1H-pyrazol-4-yl)-N4-methyl-5-(trifluoromethyl)pyrimidine-2,4-diamine;

N2-(1-(3-fluorotetrahydro-2H-pyran-4-yl)-3-methyl-1H-pyrazol-4-yl)-N4-methyl-5-(trifluoromethyl)pyrimidine-2,4-diamine;

N2-(1-(3-fluorotetrahydro-2H-pyran-4-yl)-5-methyl-1H-pyrazol-4-yl)-N4-methyl-5-(trifluoromethyl)pyrimidine-2,4-diamine;

N2-(1-((3R)-3-fluorotetrahydro-2H-pyran-4-yl)-5-methyl-1H-pyrazol-4-yl)-N4-methyl-5-(trifluoromethyl)pyrimidine-2,4-diamine 3-methyl-3-(3-methyl-4-((4-(methylamino)-5-(trifluoromethyl)pyrimidin-2-yl)amino)-1H-pyrazol-1-yl)butanenitrile;

2-((3-methyl-4-((4-(methylamino)-5-(trifluoromethyl)pyrimidin-2-yl)amino)-1H-pyrazol-1-yl)methyl)butanenitrile;

3-methyl-3-(3-methyl-4-((4-(methylamino)-5-(trifluoromethyl)pyrimidin-2-ylamino)-1H-pyrazol-1-yl)butanenitrile;

2-(5-((4-(ethylamino)-5-(trifluoromethyl)pyrimidin-2-yl)amino)-1-methyl-1H-pyrazol-3-yl)-2-methylpropanenitrile;

2-methyl-2-(1-methyl-5-((4-(methylamino)-5-(trifluoromethyl)pyrimidin-2-yl)amino)-1H-pyrazol-3-yl)propanenitrile;

2-((1-(2-cyanopropan-2-yl)-3-methyl-1H-pyrazol-4-yl)amino)-4-(cyclopropylamino)pyrimidine-5-carbonitrile;

2-((1-(2-cyanopropan-2-yl)-3-methyl-1H-pyrazol-4-yl)amino)-4-(cyclopropylamino)pyrimidine-5-carbonitrile;

2-((1-(2-cyanopropan-2-yl)-3-methyl-1H-pyrazol-4-yl)amino)-4-(ethylamino)pyrimidine-5-carbonitrile;

2-methyl-2-(3-methyl-4-((4-(methylamino)-5-(trifluoromethyl)pyrimidin-2-yl)amino)-1H-pyrazol-1-yl)butanenitrile; and 5-((4-(ethylamino)-5-(trifluoromethyl)pyrimidin-2-yl)amino)-1-methyl-1H-pyrazole-3-carbonitrile.

In one aspect of the invention there is provided a compound selected from:

$N^2$-(1',5-dimethyl-1'H-1,4'-bipyrazol-4-yl)-N4-methyl-5-(trifluoromethyl)pyrimidine-2,4-diamine;

$N^2$-(1',3-dimethyl-1'H-1,4'-bipyrazol-4-yl)-N4-methyl-5-(trifluoromethyl)pyrimidine-2,4-diamine;

4-(cyclopropylamino)-2-((5-methyl-1-(tetrahydro-2H-pyran-4-yl)-1H-pyrazol-4-yl)amino)pyrimidine-5-carbonitrile;

4-(cyclopropylamino)-2-((3-methyl-1-(tetrahydro-2H-pyran-4-yl)-1H-pyrazol-4-yl)amino)pyrimidine-5-carbonitrile;

2-((1-(1-cyanopropyl)-5-methyl-1H-pyrazol-4-yl)amino)-4-(cyclopropylamino)pyrimidine-5-carbonitrile;

N2-(1-(1-fluoro-2-methylpropan-2-yl)-3-methyl-1H-pyrazol-4-yl)-N4-methyl-5-(trifluoromethyl)pyrimidine-2,4-diamine;

2-((5-chloro-1-(tetrahydro-2H-pyran-4-yl)-1H-pyrazol-4-yl)amino)-4-(ethylamino)pyrimidine-5-carbonitrile;

5-bromo-$N^2$-(1,5-dimethyl-1H-pyrazol-4-yl)-$N^4$-methylpyrimidine-2,4-diamine;

2-methyl-2-(3-methyl-4-((4-(methylamino)-5-(trifluoromethyl)pyrimidin-2-yl)amino)-1H-pyrazol-1-yl)propan-1-ol;

1-((5-chloro-4-((4-(methylamino)-5-(trifluoromethyl)pyrimidin-2-yl)amino)-1H-pyrazol-1-yl)methyl)cyclopropanol;

N2-(3-chloro-1-(2-(4-ethyl-4H-1,2,4-triazol-3-yl)propan-2-yl)-1H-pyrazol-4-yl)-N4-methyl-5-(trifluoromethyl)pyrimidine-2,4-diamine;

N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;

N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;

N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;

N4-methyl-N2-(3-methyl-1-(3-methyloxetan-3-yl)-1H-pyrazol-4-yl)-5-(trifluoromethyl)pyrimidine-2,4-diamine;

N2-(1-(2-(1,4-dimethyl-1H-imidazol-2-yl)propan-2-yl)-3-methyl-1H-pyrazol-4-yl)-N4-methyl-5-(trifluoromethyl)pyrimidine-2,4-diamine;

N2-(1-(2-(1,4-dimethyl-1H-imidazol-2-yl)propan-2-yl)-3-methyl-1H-pyrazol-4-yl)-N4-methyl-5-(trifluoromethyl)pyrimidine-2,4-diamine;

N4-methyl-N2-(3-methyl-1-(2-(5-methyloxazol-2-yl)propan-2-yl)-1H-pyrazol-4-yl)-5-(trifluoromethyl)pyrimidine-2,4-diamine;

N4-ethyl-N2-(3-methyl-1-(3-methyloxetan-3-yl)-1H-pyrazol-4-yl)-5-(trifluoromethyl)pyrimidine-2,4-diamine;

N4-ethyl-N2-(1-((2-methoxyethyl)sulfonyl)-3-methyl-1H-pyrazol-4-yl)-5-(trifluoromethyl)pyrimidine-2,4-diamine;

N2-(1-((2-methoxyethyl)sulfonyl)-3-methyl-1H-pyrazol-4-yl)-N4-methyl-5-(trifluoromethyl)pyrimidine-2,4-diamine;

N2-(1-((2-methoxyethyl)sulfonyl)-5-methyl-1H-pyrazol-4-yl)-N4-methyl-5-(trifluoromethyl)pyrimidine-2,4-diamine;

N2-(5-chloro-1-(2-(4-methyl-4H-1,2,4-triazol-3-yl)propan-2-yl)-1H-pyrazol-4-yl)-N4-ethyl-5-(trifluoromethyl)pyrimidine-2,4-diamine;

N4-methyl-N2-(5-methyl-1-(2-(1-methyl-1H-pyrazol-3-yl)propyl)-1H-pyrazol-4-yl)-5-(trifluoromethyl)pyrimidine-2,4-diamine;

N4-methyl-N2-(5-methyl-1-(2-(1-methyl-1H-pyrazol-3-yl)propyl)-1H-pyrazol-4-yl)-5-(trifluoromethyl)pyrimidine-2,4-diamine;

N4-methyl-N2-(3-methyl-1-(2-(pyrimidin-2-yl)propan-2-yl)-1H-pyrazol-4-yl)-5-(trifluoromethyl)pyrimidine-2,4-diamine;

N2-(3-chloro-1-(2-(5-methyl-1,3,4-oxadiazol-2-yl)propan-2-yl)-1H-pyrazol-4-yl)-N4-ethyl-5-(trifluoromethyl)pyrimidine-2,4-diamine;

$N^4$-ethyl-$N^2$-(3-methyl-1-(2-(5-methyl-1,3,4-oxadiazol-2-yl)propan-2-yl)-1H-pyrazol-4-yl)-5-(trifluoromethyl)pyrimidine-2,4-diamine;

N4-ethyl-N2-(1-(2-(5-ethyl-1,3,4-oxadiazol-2-yl)propan-2-yl)-3-methyl-1H-pyrazol-4-yl)-5-(trifluoromethyl)pyrimidine-2,4-diamine;

N4-ethyl-N2-(1-(2-(1-isopropyl-1H-1,2,4-triazol-3-yl)propan-2-yl)-3-methyl-1H-pyrazol-4-yl)-5-(trifluoromethyl)pyrimidine-2,4-diamine;

N2-(3-chloro-1-(2-(4-methyl-4H-1,2,4-triazol-3-yl)propan-2-yl)-1H-pyrazol-4-yl)-N4-ethyl-5-(trifluoromethyl)pyrimidine-2,4-diamine;

N2-(3-chloro-1-(2-(1-methyl-1H-1,2,4-triazol-3-yl)propan-2-yl)-1H-pyrazol-4-yl)-N4-ethyl-5-(trifluoromethyl)pyrimidine-2,4-diamine;

N4-methyl-N2-(5-methyl-1-(2-(1-methyl-1H-pyrazol-3-yl)ethyl)-1H-pyrazol-4-yl)-5-(trifluoromethyl)pyrimidine-2,4-diamine;

N4-ethyl-N2-(3-methyl-1-(2-(1-methyl-1H-pyrazol-3-yl)propan-2-yl)-1H-pyrazol-4-yl)-5-(trifluoromethyl)pyrimidine-2,4-diamine;

N4-ethyl-N2-(3-methyl-1-(2-(1-methyl-1H-pyrazol-5-yl)propan-2-yl)-1H-pyrazol-4-yl)-5-(trifluoromethyl)pyrimidine-2,4-diamine;

N4-methyl-N2-(3-methyl-1-(2-(1-methyl-1H-pyrazol-3-yl)ethyl)-1H-pyrazol-4-yl)-5-(trifluoromethyl)pyrimidine-2,4-diamine;

N2-(1-(3-fluorotetrahydro-2H-pyran-4-yl)-3-methyl-1H-pyrazol-4-yl)-N4-methyl-5-(trifluoromethyl)pyrimidine-2,4-diamine;

N2-(1-(3-fluorotetrahydro-2H-pyran-4-yl)-3-methyl-1H-pyrazol-4-yl)-N4-methyl-5-(trifluoromethyl)pyrimidine-2,4-diamine;

N2-(1-(3-fluorotetrahydro-2H-pyran-4-yl)-5-methyl-1H-pyrazol-4-yl)-N4-methyl-5-(trifluoromethyl)pyrimidine-2,4-diamine;

N2-(1-((3R)-3-fluorotetrahydro-2H-pyran-4-yl)-5-methyl-1H-pyrazol-4-yl)-N4-methyl-5-(trifluoromethyl)pyrimidine-2,4-diamine 3-methyl-3-(3-methyl-4-((4-(methylamino)-5-(trifluoromethyl)pyrimidin-2-yl)amino)-1H-pyrazol-1-yl)butanenitrile;

2-((3-methyl-4-((4-(methylamino)-5-(trifluoromethyl)pyrimidin-2-yl)amino)-1H-pyrazol-1-yl)methyl)butanenitrile;

3-methyl-3-(3-methyl-4-(4-(methylamino)-5-(trifluoromethyl)pyrimidin-2-ylamino)-1H-pyrazol-1-yl)butanenitrile;

2-(5-((4-(ethylamino)-5-(trifluoromethyl)pyrimidin-2-yl)amino)-1-methyl-1H-pyrazol-3-yl)-2-methylpropanenitrile;

2-methyl-2-(1-methyl-5-(4-(methylamino)-5-(trifluoromethyl)pyrimidin-2-yl)amino)-1H-pyrazol-3-yl)propanenitrile;

2-((1-(2-cyanopropan-2-yl)-3-methyl-1H-pyrazol-4-yl)amino)-4-(cyclopropylamino)pyrimidine-5-carbonitrile;

2-((1-(2-cyanopropan-2-yl)-3-methyl-1H-pyrazol-4-yl)amino)-4-(cyclopropylamino)pyrimidine-5-carbonitrile;

2-((1-(2-cyanopropan-2-yl)-3-methyl-1H-pyrazol-4-yl)amino)-4-(ethylamino)pyrimidine-5-carbonitrile;

2-methyl-2-(3-methyl-4-((4-(methylamino)-5-(trifluoromethyl)pyrimidin-2-yl)amino)-1H-pyrazol-1-yl)butanenitrile; and 5-((4-(ethylamino)-5-(trifluoromethyl)pyrimidin-2-yl)amino)-1-methyl-1H-pyrazole-3-carbonitrile, or a pharmaceutical salt thereof.

The invention also provides a method for treating a disease or condition mediated by or otherwise associated with the LRRK2 receptor, the method comprising administering to a subject in need thereof an effective amount of a compound of the invention.

The disease may be a neurodegenerative disease such as Parkinson's disease, Huntington's disease or Lewie body dementia.

The disease may be a CNS disorder such as Alzheimer's disease or L-Dopa induced dyskinesia.

The disease may be a cancer or proliferative disorder such as kidney, breast, prostate, blood, papillary or lung cancer, acute myelogenous leukemia, or multiple myeloma.

The disease may be an inflammatory disease such as leprosy, Crohn's disease, amyotrophic lateral sclerosis, rheumatoid arthritis, or ankylosing spondylytis.

The invention also provides a method for enhancing cognitive memory, the method comprising administering to a subject in need thereof an effective amount of a compound of the invention.

The invention also provides a compound as described herein for use as therapeutically active substance.

The invention also provides a compound as described herein for the use as therapeutically active substance for the therapeutic and/or prophylactic treatment of Parkinson's disease.

The invention also provides a use of a compound as described herein in the therapeutic and/or prophylactic treatment of Parkinson's disease.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula I, wherein X, $R^1$, $R^2$, $R^3$, $R^4$ and $R^5$ are as defined herein.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and in some embodiments 1-30 mg daily, depending upon numerous factors such as the severity of the disease to be treated, the age and relative health

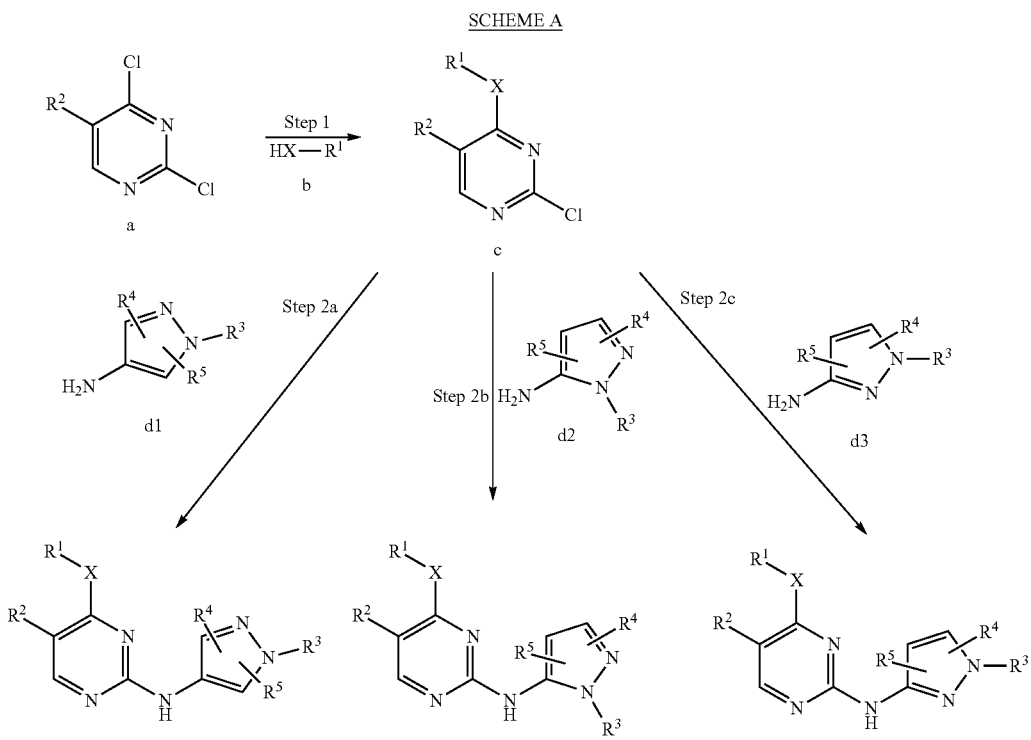

SCHEME A

In step 1 of Scheme A, dichloropyrimidine compound a is reacted with reagent b to afford pyrimidine compound c. The reaction of step 1 may take place under polar solvent conditions. In embodiments of the invention where X is —O— (reagent b is an alcohol), the reaction of step 1 may be carried out in the presence of base.

Following step 1, one of steps 2a, 2b and 2c is carried out. In step 2a, pyrimidine compound c undergoes reaction with 4-amino-pyrazole compound d1 to provide an aminopyrimidine compound of formula III. In step 2b, pyrimidine compound c is reacted with 5-amino-pyrazole compound d2 to afford an aminopyrimidine compound of formula IV. In step 2c, pyrimidine compound c is treated with 3-amino-pyrazole compound d3 to yield an aminopyrimidine compounds in accordance with the invention. The reaction of steps 2a-2c may take place in polar protic solvent and in the presence of acid such as HCl.

Many variations on the procedure of Scheme A are possible and will suggest themselves to those skilled in the art. Specific details for producing compounds of the invention are described in the Examples below.

of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of LRRK2-mediated diseases or conditions, including neurodegenerative diseases such as Parkinson's disease, Lewy body dementia and Huntington's disease, and for enhancement of cognitive memory generally in subjects in need thereof.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

ABBREVIATIONS

AcOH Acetic acid
AIBN 2,2'-Azobis(2-methylpropionitrile)
Atm. Atmosphere
$(BOC)_2O$ di-tert-Butyl dicarbonate
dba tris(dibenzylideneacetone)
DCM Dichloromethane/Methylene chloride
DIAD Diisopropyl azodicarboxylate
DIPEA Diisopropylethylamine
DMAP 4-Dimethylaminopyridine
DME 1,2-Dimethoxyethane
DMF N,N-Dimethylformamide
DMSO Dimethyl sulfoxide
DPPF 1,1'-Bis(diphenylphosphino)ferrocene
$Et_2O$ Diethyl ether
EtOH Ethanol/Ethyl alcohol
EtOAc Ethyl acetate
HATU 2-(1H-7-Azabenzotriazol-1-yl)-1,1,3,3-tetramethyl uronium hexafluorophosphate Methanaminium
HBTU O-Benzotriazol-1-yl-N,N,N',N'-tetramethyluronium hexafluorophosphate
HOBT 1-Hydroxybenzotriazole
HPLC High pressure liquid chromatography
RP HPLC Reverse phase high pressure liquid chromatography
i-PrOH Isopropanol/isopropyl alcohol
LCMS Liquid Chromatograph/Mass Spectroscopy
MeOH Methanol/Methyl alcohol
MW Microwaves
NBS N-Bromosuccinimide
NMP 1-Methyl-2-pyrrolidinone
PSI Pound per square inch
RT Room temperature
SFC Supercritical fluid chromatography
TBDMS tert-Butyldimethylsilyl
TFA Trifluoroacetic acid
THF Tetrahydrofuran
TLC Thin layer chromatography
Xphos 2-Dicyclohexylphosphino-2',4',6'-triisopropylbiphenyl Liquid Chromatography-Mass Spectrometry Method A LC-MS was performed on an Agilent 1200 Series LC coupled to an Agilent 6140 quadrupole mass spectrometer using an Agilent SD-C18 column (1.8 µm, 2.1×30 mm) with a linear gradient of 3-95% acetonitrile/water (with 0.05% trifluoroacetic acid in each mobile phase) within 8.5 minutes and held at 95% for 2.5 minutes.

Liquid Chromatography-Mass Spectrometry Method B

LC-MS was performed on a Waters 2795 Alliance HT HPLC with Waters 2996 Diode Array Detector coupled to a Micromass ZQ, single quadrapole mass spectrometer using a Phenomenex Luna C18 (2) column (5 um, 100×4.6 mm plus guard cartridge) with a linear gradient of 5-95% acetonitrile/water (with 0.1% formic acid in each mobile phase) within 3.5 minutes and held at 95% for 2.0 minutes.

Liquid Chromatography-Mass Spectrometry Method C

LC-MS was performed on a Waters 2795 Alliance HT HPLC with Waters 2996 Diode Array Detector coupled to a Micromass ZQ, single quadrapole mass spectrometer using a Waters Xterra MS C18 column (5 um, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.

Analytical Methods $^1$H Nuclear magnetic resonance (NMR) spectroscopy was carried out using a Bruker instrument operating at 400 or 500 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad. Where thin layer chromatography (TLC) has been used it refers to silica gel TLC using silica gel MK6F 60 Å plates, $R_f$ is the distance travelled by the compound divided by the distance travelled by the solvent on a TLC plate. Flash chromatography refers to silica gel chromatography and is carried out using an SP4 or an Isolara 4 MPLC system (manufactured by Biotage); pre-packed silica gel cartridges (supplied by Biotage); or using conventional glass column chromatography.

Compound Preparation

Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is an Initiator 60 supplied by Biotage. The actual power supplied varies during the course of the reaction in order to maintain a constant temperature.

Compounds made in the following examples are summarized in the Tables below, which shows affinity values for LRRK2 (Ki, micromolar) for representative compounds together with LCMS method (M), LC retention time (RT) in minutes, and Mass Spec m/z values (molecular weight).

Intermediate 1

2,5-Dichloro-N-methylpyrimidin-4-amine

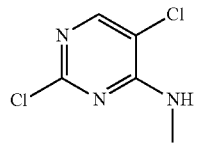

To a cooled (0° C.) solution of 2,4,5-trichloropyrimidine (2.0 g, 11 mmol) in methanol (30 mL) was added dropwise a 2 M solution of methylamine in methanol (6.3 mL). The reaction was allowed to warm to room temperature and stirred overnight. The reaction was then concentrated and redissolved in DCM. The solution was washed with sat. NaHCO$_3$, brine, dried over Na$_2$SO$_4$, filtered and concentrated. The crude product was purified by column chromatography (0-40% EtOAc in heptane) to give 2,5-dichloro-N-methylpyrimidin-4-amine (0.9 g, 50%). $^1$H-NMR (DMSO): δ 8.13 (s, 1H), 7.89 (s, 1H), 2.86 (d, J=4.5, 3H).

Intermediate 2

5-Bromo-2-chloro-N-methylpyrimidin-4-amine

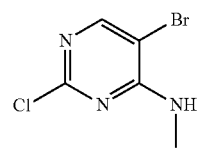

To a cooled (0° C.) solution of 5-bromo-2,4-dichloropyrimidine (5.0 g, 22 mmol) in methanol (42 mL) was added dropwise a 33 wt % solution of methylamine in ethanol (3.3 mL). The reaction was allowed to warm to room temperature. The reaction was then concentrated. The crude product was purified by column chromatography (0-10% methanol in DCM) to give 5-bromo-2-chloro-N-methylpyrimidin-4-amine (1.8 g, 39%). $^1$H-NMR (DMSO): δ 8.22 (s, 1H), 7.75 (s, 1H), 2.85 (d, J=3.9, 3H).

Intermediate 3

2-Chloro-N-methyl-5-(trifluoromethyl)pyrimidin-4-amine

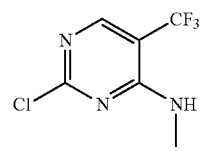

To a cooled (−10° C.) solution of 2,4-dichloro-5-trifluoromethylpyrimidine (20 g, 0.089 mol) in methanol (100 mL) was added triethylamine (12.5 mL, 0.089 mol) and a 2 M solution of methylamine in methanol (45 mL). The reaction was allowed to warm to room temperature and stirred overnight. The reaction was then concentrated and re-dissolved in ethyl acetate. The solution was washed with sat. NaHCO$_3$, brine, dried over MgSO$_4$, filtered and concentrated. The crude product was purified by column chromatography (5-25% EtOAc in heptane) to give 2-chloro-N-methyl-5-(trifluoromethyl)pyrimidin-4-amine (8.6 g, 45%). $^1$H-NMR (DMSO): δ 8.37 (s, 1H), 7.90 (s, 1H), 2.90 (s, 3H).

Additional intermediates prepared using similar methods as described above are listed in Table 1 below:

TABLE 1

| 4 | 2-chloro-N-ethyl-5-(trifluoromethyl)pyrimidin-4-amine | 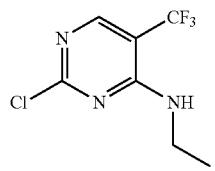 |
|---|---|---|

TABLE 1-continued

| | | |
|---|---|---|
| 5 | 2,5-dichloro-4-ethoxypyrimidine | 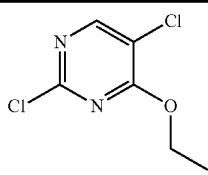 |
| 6 | 2-chloro-N-cyclopropyl-5-(trifluoromethyl)pyrimidin-4-amine | 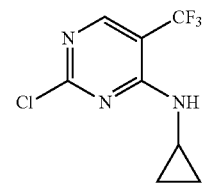 [SMILES: FC(F)(F)c1cnc(Cl)nc1NC1CC1] |
| 7 | 2-chloro-4-(methylamino)pyrimidine-5-carbonitrile | 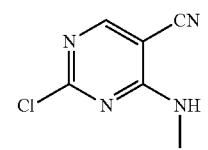 |

Intermediate 8 and 9

1',5-dimethyl-1'H-1,4'-bipyrazol-4-amine and 1',3-dimethyl-1'H-1,4'-bipyrazol-4-amine

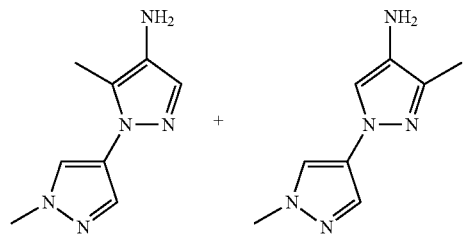

Step 1—1',5-dimethyl-4-nitro-1'H-1,4'-bipyrazole and 1',3-dimethyl-4-nitro-1'H-1,4'-bipyrazole To a suspension of 3-methyl-4-nitro-1H-pyrazole (350 mg, 2.76 mmol), 1-methyl-4-(4,4,5,5-tetramethyl-1,3,2-dioxaborolan-2-yl)-1H-pyrazole (859 mg, 4.13 mmol), and copper(II) acetate (150 mg, 0.825 mmol) in DMF (8 mL) was added pyridine (87 mg 1.1 mmol). The mixture was stirred at 95° C. under oxygen for 12 h. The reaction mixture was diluted with water and extracted with EtOAc (30 mL×3). The combined extracts were washed with brine, dried over $Na_2SO_4$, filtered, and concentrated. The residue was purified by silica gel column chromatography eluting with ethyl acetate/petroleum ether (1/5) to give a mixture of two regioisomers (71 mg, 13%) as an off white solid.

Step 2—1',5-dimethyl-1'H-1,4'-bipyrazol-4-amine and 1',3-dimethyl-1'H-1,4'-bipyrazol-4-amine A suspension of the mixture of 1',5-dimethyl-4-nitro-1'H-1,4'-bipyrazole and 1',3-dimethyl-4-nitro-1'H-1,4'-bipyrazole (71 mg, 0.34 mmol) and 10% Pd/C (50 mg) in methanol (10 mL) was stirred at 55° C. under $H_2$ for 3 h. The insoluble material was filtered off and the filtrate was concentrated under reduced pressure to afford the two title compounds as a mixture (50 mg, 83%).

Intermediate 10

1-(3-fluoro-tetrahydro-2H-pyran-4-yl)-3-methyl-1H-pyrazol-4-amine

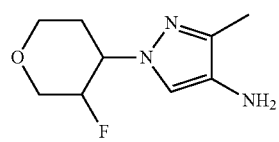

Step 1—3-fluoro-tetrahydro-2H-pyran-4-ol $NaBH_4$ (190 mg, 5.00 mmol) was added to the mixture of 3-fluoro-tetrahydropyran-4-one (300 mg, 2.50 mmol) in $CH_3CN$ (3 mL). After being stirred at 20° C. for 10 h, $H_2O$ (10 mL) was added. The resulting mixture was extracted with ethyl acetate (20 mL×3), dried over sodium sulfate, and concentrated under reduced pressure to afford the title compounds (200 mg, 62%) as oil.

Step 2—3-fluoro-tetrahydro-2H-pyran-4-yl methanesulfonate

MSCl (189 mg, 1.65 mmol) was added to a mixture of 3-fluoro-tetrahydro-2H-pyran-4-ol (180 mg, 1.5 mmol) and triethylamine (0.5 mL) at 0° C. The solution were stirred at room temperature for 4 h, $H_2O$ (10 mL) was added to quench the reaction. The resulting mixture was extracted with ethyl acetate (20 mL×3), dried over sodium sulfate, and concentrated under reduced pressure to afford the title compounds (300 mg, 91%) as oil.

Step 3—1-(3-fluoro-tetrahydro-2H-pyran-4-yl)-3-methyl-4-nitro-1H-pyrazole

A mixture of 3-fluoro-tetrahydro-2H-pyran-4-yl methanesulfonate (60 mg, 0.50 mmol), 3-methyl-4-nitro-1H-pyrazole (98 mg, 0.50 mmol), and $Cs_2CO_3$ (243 mg, 0.750 mmol) in DMF (2.0 mL) was stirred at 100° C. for 2 h. After cooling down, the resulting mixture was extracted with ethyl acetate (20 mL×3), washed with $H_2O$ (20 mL). The organic layers were combined, washed with brine (20 mL), dried over sodium sulfate, and concentrated under reduced pressure to afford the title compounds (60 mg, 56%) as oil. LC-MS (ESI): m/z=230 $(M+H)^+$.

Step 4—1-(3-fluoro-tetrahydro-2H-pyran-4-yl)-3-methyl-1H-pyrazol-4-amine

A mixture of 1-(3-fluoro-tetrahydro-2H-pyran-4-yl)-3-methyl-4-nitro-1H-pyrazole (60 mg, 0.26 mmol) and 10% Pd/C (30 mg) in methanol (5 mL) was stirred under $H_2$ at room temperature for 5 h. The insoluble material was filtered off and the filtrate was concentrated under reduced pressure to afford the title compound (40 mg, 77%) as oil. LC-MS (ESI): m/z=200 (M+H)$^+$.

Intermediates 11 and 12

3-methyl-1-(2-(1-methyl-1H-pyrazol-3-yl)ethyl)-1H-pyrazol-4-amine and 5-methyl-1-(2-(1-methyl-1H-pyrazol-3-yl)ethyl)-1H-pyrazol-4-amine

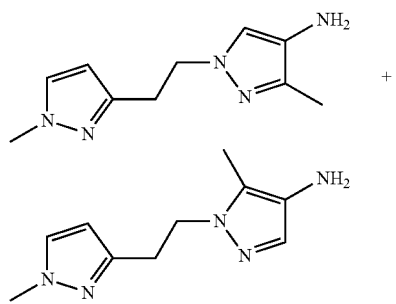

Step 1—2-(1H-pyrazol-3-yl)acetohydrazide

A solution of 5-nitropyridin-2-ol (5.0 g, 36 mmol) in hydrazine hydrate (20 mL) was stirred at 100° C. for 3 h. After cooling down, the mixture was concentrated to afford the title compound (5.0 g, 100%) as red oil. LC-MS (ESI): m/z=141 (M+H)$^+$.

Step 2—2-(1H-pyrazol-3-yl)acetic acid

A solution of 2-(1H-pyrazol-3-yl)acetohydrazide (5.0 g, 36 mmol) in con. HCl (200 mL) was stirred at 100° C. for 3 h. The insoluble materials were filtered off, the filtrate was concentrated to give the title compound (4.0 g, 89%) as a yellow solid. LC-MS (ESI): m/z=127 (M+H)$^+$.

Step 3—ethyl 2-(1H-pyrazol-3-yl)acetate

A solution of 2-(1H-pyrazol-3-yl)acetic acid (4.0 g, 32 mmol) and conc. H$_2$SO$_4$ (1.0 mL) in ethanol (100 mL) was refluxed overnight. After concentration, the residue was treated with aq. NaHCO$_3$, extracted with ethyl acetate, dried over Na$_2$SO$_4$. Removal of the solvent gave the title compound (4.6 g, 94%) as brown oil. LC-MS (ESI): m/z=155 (M+H)$^+$.

Step 4—ethyl 2-(1-methyl-1H-pyrazol-3-yl)acetate

To a mixture of ethyl 2-(1H-pyrazol-3-yl)acetate (1.0 g, 6.5 mmol) and Cs$_2$CO$_3$ (4.2 g, 13 mmol) in DMF (5 mL) was added iodomethane (1.84 g, 13.0 mmol). The mixture was stirred at 0° C. for 6 h. H$_2$O (20 ml) was then added and the resulting mixture was extracted with EtOAc (20 ml×3). The organic layers were combined, washed with brine (20 ml), dried over sodium sulfate, and concentrated under reduced pressure to afford the title compound (600 mg, 55%) as yellow oil. LC-MS (ESI): m/z=169 (M+H)$^+$.

Step 5—2-(1-methyl-1H-pyrazol-3-yl)ethanol

To a solution of ethyl 2-(1-methyl-1H-pyrazol-3-yl)acetate (600 mg, 3.57 mmol) in THF (10 ml) was added borane-tetrahydrofuran complex (10 ml, 1.0 M). The mixture was stirred at room temperature for 12 h. CH$_3$OH (10 ml) and H$_2$O (10 ml) were added and the resulting mixture was extracted with EtOAc (20 ml×3). The organic layers were combined, washed with brine (20 ml), dried over sodium sulfate, and concentrated under reduced pressure to afford the title compound (400 mg, 89%) as yellow oil. LC-MS (ESI): m/z=127 (M+H)$^+$.

Step 6—2-(1-methyl-1H-pyrazol-3-yl)ethyl methanesulfonate

To a mixture of 2-(1-methyl-1H-pyrazol-3-yl)ethanol (400 mg, 3.18 mmol), Et$_3$N (641 mg, 6.35 mmol) in CH$_2$Cl$_2$ (20 ml) was added mesyl chloride (579 mg, 5.08 mmol) dropwise at 0° C. After being stirred at room temperature overnight, the mixture was diluted with CH$_2$Cl$_2$, washed with aq. NaHCO$_3$, dried over Na$_2$SO$_4$. Removal of the solvent afforded the title compound (600 mg, 93%) as yellow oil. LC-MS (ESI): m/z=205 (M+H)$^+$.

Step 7—3-methyl-1-(2-(1-methyl-1H-pyrazol-3-yl)ethyl)-4-nitro-1H-pyrazole and 5-methyl-1-(2-(1-methyl-1H-pyrazol-3-yl)ethyl)-4-nitro-1H-pyrazole A mixture of 2-(1-methyl-1H-pyrazol-3-yl)ethyl methanesulfonate (600 mg, 2.94 mmol), 3-methyl-4-nitro-1H-pyrazole (373 mg, 2.94 mmol), and Cs$_2$CO$_3$ (1.92 g, 5.882 mmol) in DMF (20 ml) was stirred at 100° C. for 2 h. H$_2$O (20 ml) was added and the resulting mixture was extracted with EtOAc (20 ml×3). The organic layers were combined, washed with brine (20 ml), dried over sodium sulfate, and concentrated under reduced pressure. The residue was purified by prep-TLC eluting with petroleum ether/ethyl acetate (1/1) to afford the title compound (600 mg, 87%) as a white solid. LC-MS (ESI): m/z=236 (M+H)$^+$.

Step 8—3-methyl-1-(2-(1-methyl-1H-pyrazol-3-yl)ethyl)-1H-pyrazol-4-amine and 5-methyl-1-(2-(1-methyl-1H-pyrazol-3-yl)ethyl)-1H-pyrazol-4-amine To a mixture of 3-methyl-1-(2-(1-methyl-1H-pyrazol-3-yl)ethyl)-4-nitro-1H-pyrazole and 5-methyl-1-(2-(1-methyl-1H-pyrazol-3-yl)ethyl)-4-nitro-1H-pyrazole (300 mg, 1.28 mmol) in methanol (25 ml) was added 10% Pd/C (30 mg). The reaction mixture was stirred under H$_2$ at room temperature for 1 h. The insoluble material was filtered off and the filtrate was concentrated under reduced pressure to afford the title compound (260 mg, 99%) as a white solid. LC-MS (ESI): m/z=206 (M+H)$^+$.

Intermediate 13

3-methyl-1-(3-methyloxetan-3-yl)-1H-pyrazol-4-amine

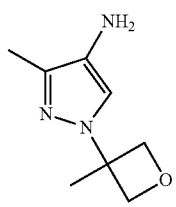

Step 1—diethyl 2-methyl-2-(3-methyl-4-nitro-1H-pyrazol-1-yl)malonate

To a solution of 3-methyl-4-nitro-1H-pyrazole (3.81 g, 30.0 mmol) in DMF (20 mL) was added K₂CO₃ (8.28 g, 60.0 mmol) and diethyl 2-bromo-2-methylmalonate (9.10 g, 36.0 mmol). The mixture was stirred at 100° C. for 20 h. The reaction mixture was then treated with H₂O (500 mL), extracted with ethyl acetate (20 mL×3). The organic layer was evaporated and the residue was purified by silica gel column chromatography eluting with petroleum ether/ethyl acetate (10/1) to afford the title compound (3.6 g, 41%) as oil. LC-MS (ESI): m/z=300 (M+H)⁺.

Step 2—2-methyl-2-(3-methyl-4-nitro-1H-pyrazol-1-yl)propane-1,3-diol

To a solution of diethyl 2-methyl-2-(3-methyl-4-nitro-1H-pyrazol-1-yl)malonate (3588 mg, 12.00 mmol) in methanol (50 mL) was added NaBH₄ (890 mg, 24.0 mmol). After being stirred at 20° C. for 2 h, the reaction was quenched H₂O (500 mL) and extracted with ethyl acetate (20 mL×3). The organic phase was evaporated and the residue was purified by silica gel column chromatography eluting with petroleum ether/ethyl acetate (5/1) to afford the title compound (900 mg, 35%) as a yellow solid. LC-MS (ESI): m/z=216 (M+H)⁺.

Step 3—3-hydroxy-2-methyl-2-(3-methyl-4-nitro-1H-pyrazol-1-yl)propyl 4-methylbenzenesulfonate To a solution of 2-methyl-2-(3-methyl-4-nitro-1H-pyrazol-1-yl)propane-1,3-diol (860 mg, 4.00 mmol) in pyridine (10 mL) was added 4-methylbenzene-1-sulfonyl chloride (760 mg, 4.00 mmol). The mixture was then refluxed for 20 h. After cooling down, the mixture was concentrated. The residue was purified by silica gel column chromatography eluting with petroleum ether/ethyl acetate (5/1) to afford the title compound (670 mg, 45%) as a white solid. LC-MS (ESI): m/z=370 (M+H)⁺.

Step 4—3-methyl-1-(3-methyloxetan-3-yl)-4-nitro-1H-pyrazole

To a solution of 3-hydroxy-2-methyl-2-(3-methyl-4-nitro-1H-pyrazol-1-yl)propyl 4-methylbenzenesulfonate (660 mg, 1.80 mmol) in THF (5 mL) was NaH (90 mg, 60%, 2.2 mmol) at 0° C. The mixture was then heated to reflux for 2 h. After cooling down, the mixture was treated with H₂O (1 mL). After concentration, the residue was purified by silica gel column chromatography eluting with petroleum ether/ethyl acetate (10/1) to afford the title compound (280 mg, 80%) as a white solid. LC-MS (ESI): m/z=198 (M+H)⁺.

Step 5—3-methyl-1-(3-methyloxetan-3-yl)-1H-pyrazol-4-amine

To a solution of 3-methyl-1-(3-methyloxetan-3-yl)-4-nitro-1H-pyrazole (275 mg, 1.40 mmol) in methanol (5 mL) was added Raney Ni (20 mg) and hydrazine hydrate (80%, 2.0 mL). The mixture was stirred at room temperature for 2 h. The insoluble material was filtered off and the filtrate was concentrated to afford the title compound (220 mg, 94%) as a yellow solid. LC-MS (ESI): m/z=168 (M+H)⁺.

Intermediates 14 and 15

3-chloro-1-(2-(4-methyl-4H-1,2,4-triazol-3-yl)propan-2-yl)-1H-pyrazol-4-amine and 3-chloro-1-(2-(1-methyl-1H-1,2,4-triazol-3-yl)propan-2-yl)-1H-pyrazol-4-amine

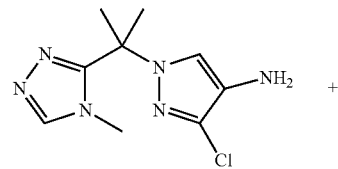

+

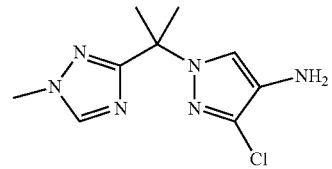

Step 1—ethyl 2-(3-chloro-4-nitro-1H-pyrazol-1-yl)-2-methylpropanoate

To a solution of 3-chloro-4-nitro-1H-pyrazole (1.0 g, 6.8 mmol) in DMF (30 mL) was added ethyl 2-bromo-2-methylpropanoate (2.00 g, 10.2 mmol) and Cs₂CO₃ (4.40 g, 13.6 mmol). The mixture was stirred at 100° C. for 2 h. After filtration, the solution was poured into water and extracted with ethyl acetate for 3 times. The organic layers were combined and dried over anhydrous Na₂SO₄. The solvent was evaporated in vacuo, the residue was purified by silica gel column chromatography to afford the title compound (1.2 g, 68%) as yellowish oil. LC-MS (ESI): m/z=262.0 (M+H)⁺.

Step 2—2-(3-chloro-4-nitro-1H-pyrazol-1-yl)-2-methylpropanoic acid

To a solution of ethyl 2-(3-chloro-4-nitro-1H-pyrazol-1-yl)-2-methylpropanoate (1.0 g, 3.8 mmol) in THF (5 mL) was added LiOH (500 mg, 22.8 mL), iPrOH (5 mL), and H₂O (5 mL). The mixture was refluxed for 2 h. The solution was evaporated in vacuo. The resulting mixture was extracted with ethyl acetate for 3 times. The organic layers were combined and dried over anhydrous Na₂SO₄. Removal of the solvent give the title compound (850 mg, 95% yield) as a white solid. LC-MS (ESI): m/z=234.1 (M+H)⁺.

Step 3—2-(3-chloro-4-nitro-1H-pyrazol-1-yl)-2-methylpropanamide

To a solution of 2-(3-chloro-4-nitro-1H-pyrazol-1-yl)-2-methylpropanoic acid (800 mg, 3.40 mmol) in DCM (10 mL)

was added SOCl$_2$ (500 mg, 22.8 mL) and DMF (a drop). The mixture was refluxed at 50° C. for 2 h. The solvent was evaporated in vacuo. To the resulting residue in DCM (10 mL) was added NH$_4$OH (2 mL). The solution was stirred at room temperature for 0.5 h. After the solvent was evaporated in vacuo, the resulting residue was purified by silica gel column chromatography eluting with petroleum ether/ethyl acetate (10:1) to afford the title compound (650 mg, 81%) as a white solid. LC-MS (ESI): m/z=233.2 (M+H)$^+$.

Step 4—(Z)-2-(3-chloro-4-nitro-1H-pyrazol-1-yl)-N-((dimethylamino)methylene)-2-methyl-propanamide A mixture of 2-(3-chloro-4-nitro-1H-pyrazol-1-yl)-2-methylpropanamide (250 mg, 1.10 mmol) in DMF-DMA (1.5 mL) was stirred at 95° C. for 2 h. Removal of the solvent afforded the title compound (250 mg, 79%). LC-MS (ESI): m/z=288.1 (M+H)$^+$.

Step 5—3-(2-(3-chloro-4-nitro-1H-pyrazol-1-yl)propan-2-yl)-4H-1,2,4-triazole

To a solution of (Z)-2-(3-chloro-4-nitro-1H-pyrazol-1-yl)-N-((dimethylamino)methylene)-2-methyl-propanamide (250 mg, 0.867 mmol) in AcOH (1.5 mL) was added hydrazine (aqueous, 85%, 1.0 mL). The mixture was stirred at 95° C. for 1.5 h. Then sat.NaHCO$_3$ was added, the mixture was extracted with ethyl acetate for 3 times. The organic layers were combined and dried over anhydrous Na$_2$SO$_4$. Removal of the solvent afforded the title compound (250 mg, 97%) as yellow oil. LC-MS (ESI): m/z=257.2 (M+H)$^+$.

Step 6—3-(2-(3-chloro-4-nitro-1H-pyrazol-1-yl)propan-2-yl)-4-methyl-4H-1,2,4-triazole and 3-(2-(3-chloro-4-nitro-1H-pyrazol-1-yl)propan-2-yl)-1-methyl-1H-1,2,4-triazole To a solution of 3-(2-(3-chloro-4-nitro-1H-pyrazol-1-yl)propan-2-yl)-4H-1,2,4-triazole (250 mg, 0.972 mmol) in CH$_3$CN (10 mL) was added Cs$_2$CO$_3$ (650 mg, 2.00 mmol) and MeI (280 mg, 2.00 mmol). The mixture was stirred at room temperature for 2 h. After concentration, the residue was purified by silica gel column chromatography eluting with petroleum ether/ethyl acetate (5/1) to afford the title compounds (235 mg, 87%) as colorless oil. LC-MS (ESI): m/z=271.2 (M+H)$^+$.

Step 7—3-chloro-1-(2-(4-methyl-4H-1,2,4-triazol-3-yl)propan-2-yl)-1H-pyrazol-4-amine and 3-chloro-1-(2-(1-methyl-1H-1,2,4-triazol-3-yl)propan-2-yl)-1H-pyrazol-4-amine To a solution of the mixture of 3-(2-(3-chloro-4-nitro-1H-pyrazol-1-yl)propan-2-yl)-4-methyl-4H-1,2,4-triazole and 3-(2-(3-chloro-4-nitro-1H-pyrazol-1-yl)propan-2-yl)-1-methyl-1H-1,2,4-triazole (100 mg, 0.370 mmol) in EtOH (2 mL) was added Zn (1.0 g) in sat. NH$_4$Cl (2.0 mL). The mixture was stirred at room temperature for 1 h. After filtration, the solvent was evaporated in vacuo. The residue was re-solved in DCM and the mixture was filtered again. The filtrate was concentrated to afford the title compounds (80 mg, 90%). LC-MS (ESI): m/z=241.2 (M+H)$^+$.

Intermediate 16

3-methyl-1-(2-(5-methyl-1,3,4-oxadiazol-2-yl)propan-2-yl)-1H-pyrazol-4-amine

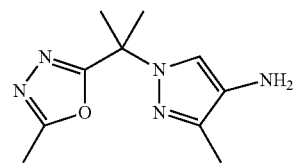 [SMILES: Cc1nnc(C(C)(C)n2cc(N)c(C)n2)o1]

Step 1—N'-acetyl-2-methyl-2-(3-methyl-4-nitro-1H-pyrazol-1-yl)propanehydrazide

To a mixture of 2-methyl-2-(3-methyl-4-nitro-1H-pyrazol-1-yl)propanoic acid (500 mg, 2.38 mmol) in DCM (20 ml) was added acetohydrazide (211 mg, 2.86 mmol), HATU (1.8 g, 4.76 mmol), and DIPEA (618 mg, 4.76 mmol). The mixture was stirred at room temperature for 1 h. After concentration, the residue was purified by silica gel column chromatography eluting with petroleum ether/ethyl acetate (1/3) to give the title product (600 mg, 95%) as light yellow oil. LC-MS (ESI): m/z=270.1 (M+H)$^+$.

Step 2—2-methyl-5-(2-(3-methyl-4-nitro-1H-pyrazol-1-yl)propan-2-yl)-1,3,4-oxadiazole A mixture of N'-acetyl-2-methyl-2-(3-methyl-4-nitro-1H-pyrazol-1-yl)propanehydrazide (500 mg, 1.73 mmol) in phosphoryl trichloride (2 ml) was stirred at 100° C. for 1 h. The reaction was quenched by ice-water. The mixture was extracted with ethyl acetate. The organic layers were combined and dried over anhydrous Na$_2$SO$_4$. After the solvent was evaporated in vacuo, the resulting residue was purified by silica gel column chromatography eluting with petroleum ether/ethyl acetate (3/1) to afford the title compound (320 mg, 68%) as a white solid. LC-MS (ESI): m/z=252.3 (M+H)$^+$.

Step 3—3-methyl-1-(2-(5-methyl-1,3,4-oxadiazol-2-yl)propan-2-yl)-1H-pyrazol-4-amine To a mixture of 2-methyl-5-(2-(3-methyl-4-nitro-1H-pyrazol-1-yl)propan-2-yl)-1,3,4-oxadiazole (100 mg, 0.400 mmol) in methanol (10 ml) was added 10% Pd/C (50 mg). The reaction mixture was stirred under H$_2$ at room temperature for 2 h. The insoluble material was filtered off and the filtrate was concentrated under reduced pressure to afford the title compound (85 mg, 92%) as yellowish oil. LC-MS (ESI): m/z=222.3 (M+H)+.

Intermediate 17

1-(2-(1-isopropyl-1H-1,2,4-triazol-3-yl)propan-2-yl)-3-methyl-1H-pyrazol-4-amine

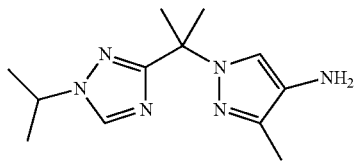 [SMILES: Cc1nn(C(C)(C)c2ncn(C(C)C)n2)cc1N]

Step 1—(Z)—N-((dimethylamino)methylene)-2-methyl-2-(3-methyl-4-nitro-1H-pyrazol-1-yl)-propanamide A solution of 2-methyl-2-(3-methyl-4-nitro-1H-pyrazol-1-yl)propanamide (1.60 g, 7.55 mmol) in DMF-DMA (8.98 g, 75.5 mmol) was stirred at 95° C. for 2 h. After cooling down, the mixture was concentrated to afford the title compound (2.10 g, over 100%). LC-MS (ESI): m/z=268 (M+H)+.

Step 2—3-(2-(3-methyl-4-nitro-1H-pyrazol-1-yl)propan-2-yl)-4H-1,2,4-triazole

A solution of (Z)—N-((dimethylamino)methylene)-2-methyl-2-(3-methyl-4-nitro-1H-pyrazol-1-yl)-propanamide (2.10 g, 7.55 mmol) and hydrazine hydrate (6.0 mL) in AcOH (15 mL) was stirred at 95° C. for 1.5 h. After cooling down, the mixture was diluted with aq. NaHCO3 and extracted with ethyl acetate. The combined extracts was washed with brine, dried over MgSO4, filtered, and concentrated to afford the title compound (1.3 g, 73% for 2 steps). LC-MS (ESI): m/z=237 (M+H)+.

Step 3—1-isopropyl-3-(2-(3-methyl-4-nitro-1H-pyrazol-1-yl)propan-2-yl)-1H-1,2,4-triazole To a solution of 3-(2-(3-methyl-4-nitro-1H-pyrazol-1-yl)propan-2-yl)-4H-1,2,4-triazole (1.3 g, 5.5 mmol) in CH3CN (30 mL) was added 2-bromopropane (813 mg, 6.60 mmol) and Cs2CO3 (1.79 g, 5.50 mmol). The mixture was stirred at 50° C. overnight. After cooling down, the mixture was diluted with water and extracted with ethyl acetate. The organic layer was concentrated to afford the title compound (1.06 g, 70%). LC-MS (ESI): m/z=279 (M+H)+.

Step 4—1-(2-(1-isopropyl-1H-1,2,4-triazol-3-yl)propan-2-yl)-3-methyl-1H-pyrazol-4-amine A mixture of 1-isopropyl-3-(2-(3-methyl-4-nitro-1H-pyrazol-1-yl)propan-2-yl)-1H-1,2,4-triazole (600 mg, 2.16 mmol) and 10% Pd/C (200 mg) in EtOH (25 mL) was stirred under hydrogen atmosphere at 50° C. for 2 h. The insoluble material was filtered off and the filtrate was evaporated to afford the title compound (420 mg, 80%). LC-MS (ESI): m/z=249 (M+H)+.

Intermediate 18

3-methyl-1-(2-(5-methyloxazol-2-yl)propan-2-yl)-1H-pyrazol-4-amine

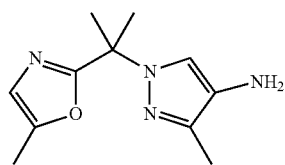 [SMILES: Cc1cnc(C(C)(C)n2cc(N)c(C)n2)o1]

Step 1—2-methyl-2-(3-methyl-4-nitro-1H-pyrazol-1-yl)-N-(prop-2-ynyl)propanamide

To a solution of 2-methyl-2-(3-methyl-4-nitro-1H-pyrazol-1-yl)propanoic acid (1.00 g, 4.69 mmol) and prop-2-yn-1-amine (387 mg, 7.04 mmol) in DCM (30 mL) was added DIPEA (908 mg, 7.04 mmol) and HTAU (2.38 g, 7.04 mmol). After being stirred at room temperature for 3 h, the mixture was extracted with DCM and washed with water. The organic layer was concentrated to afford the title compound (770 mg, 66%). LC-MS (ESI): m/z=251 (M+H)+.

Step 2—5-methyl-2-(2-(3-methyl-4-nitro-1H-pyrazol-1-yl)propan-2-yl)oxazole

A mixture of 2-methyl-2-(3-methyl-4-nitro-1H-pyrazol-1-yl)-N-(prop-2-ynyl)propanamide (500 mg, 2.00 mmol) and AuCl3 (61 mg, 0.20 mmol) in CH3CN (10 mL) was stirred at room temperature for 21 h. The insoluble material was filtered off and the filtrate was concentrated to afford the title compound (200 mg, 40%). LC-MS (ESI): m/z=251 (M+H)+.

Step 3—3-methyl-1-(2-(5-methyloxazol-2-yl)propan-2-yl)-1H-pyrazol-4-amine

A mixture of 5-methyl-2-(2-(3-methyl-4-nitro-1H-pyrazol-1-yl)propan-2-yl)oxazole (200 mg, 0.800 mmol) and 10% Pd/C (80 mg) in EtOH (10 mL) was stirred under hydrogen atmosphere at room temperature for 2 h. The insoluble material was filtered off and the filtrate was evaporated to afford the title compound (175 mg, 100%). LC-MS (ESI): m/z=221 (M+H)$^+$.

Intermediate 19

3-methyl-1-(2-(pyrimidin-2-yl)propan-2-yl)-1H-pyrazol-4-amine

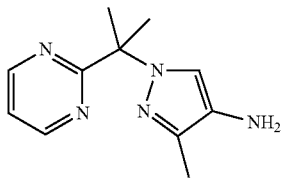 [SMILES: Cc1nn(C(C)(C)c2ncccn2)cc1N]

Step 1—2-(2-(3-methyl-4-nitro-1H-pyrazol-1-yl)propan-2-yl)pyrimidine

A solution of 2-methyl-2-(3-methyl-4-nitro-1H-pyrazol-1-yl)propanimidamide (500 mg, 2.37 mmol) and 1,1,3,3-tetramethoxypropane (1.94 mg, 11.1 mmol) in 1,4-dioxane (20 mL) was stirred at 130° C. overnight. The insoluble material was filtered off and the filtrate was concentrated. The residue was purified by silica gel column chromatography eluting with petroleum ether/ethyl acetate (3/1) to afford the title compound (220 mg, 34%). LC-MS (ESI): m/z=248 (M+H)$^+$.

Step 2—3-methyl-1-(2-(pyrimidin-2-yl)propan-2-yl)-1H-pyrazol-4-amine

A mixture of 2-(2-(3-methyl-4-nitro-1H-pyrazol-1-yl)propan-2-yl)pyrimidine (220 mg, 0.890 mmol) and 10% Pd/C (80 mg) in EtOH (10 mL) was stirred under hydrogen atmosphere at room temperature for 2 h. The insoluble material was filtered off and the filtrate was evaporated to afford the title compound (160 mg, 83%). LC-MS (ESI): m/z=218 (M+H)$^+$.

Intermediate 20

1-((4-amino-5-chloro-1H-pyrazol-1-yl)methyl)cyclopropanol

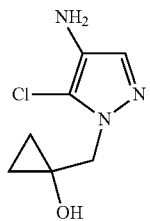 [SMILES: Nc1cnn(CC2(O)CC2)c1Cl]

Step 1—ethyl 1-(tetrahydro-2H-pyran-2-yloxy)cyclopropanecarboxylate

To a solution of ethyl 1-hydroxycyclopropanecarboxylate (1040 mg, 8.000 mmol) and PTSA (137 mg, 0.800 mmol) in DCM (20 mL) was added a solution of DHP (1344 mg, 16.00 mmol) in DCM (10 mL) dropwise at 0° C. The mixture was stirred for 20 h at room temperature. After concentration, the residue was purified by silica gel column chromatography eluting with petroleum ether/ethyl acetate (10/1) to afford the title compound (1500 mg, 85%) as oil. LC-MS (ESI): m/z=215 (M+H)$^+$.

Step 2—(1-(tetrahydro-2H-pyran-2-yloxy)cyclopropyl)methanol

To a solution of ethyl 1-(tetrahydro-2H-pyran-2-yloxy)cyclopropanecarboxylate (1500 mg, 7.000 mmol) in THF (20 mL) was added LiAlH$_4$ (532 mg, 14.0 mmol) at 0° C. After being stirred for 30 min at 0° C., the reaction was quenched with H$_2$O (1.0 mL). After concentration, the residue was purified by silica gel column chromatography eluting with petroleum ether/ethyl acetate (3/1) to afford the title compound (920 mg, 77%) as colorless oil. LC-MS (ESI): m/z=173 (M+H)$^+$.

Step 3—4-nitro-1-((1-(tetrahydro-2H-pyran-2-yloxy)cyclopropyl)methyl)-1H-pyrazole To a solution of (1-(tetrahydro-2H-pyran-2-yloxy)cyclopropyl)methanol (515 mg, 3.00 mmol), 4-nitro-1H-pyrazole (407 mg, 3.60 mmol), and PPh$_3$ (1180 mg, 4.500 mmol) in THF (10 mL) was added DIAD (606 mg, 3.00 mmol) at 0° C. The mixture was stirred at 20° C. for 20 h. After concentration, the residue was purified by silica gel column chromatography eluting with petroleum ether/ethyl acetate (4/1) to afford the title compound (186 mg, 24%) as a white solid. LC-MS (ESI): m/z=268 (M+H)$^+$.

Step 4—5-chloro-4-nitro-1-((1-(tetrahydro-2H-pyran-2-yloxy)cyclopropyl)methyl)-1H-pyrazole To a solution of 4-nitro-1-((1-(tetrahydro-2H-pyran-2-yloxy)cyclopropyl)methyl)-1H-pyrazole (186 mg, 0.700 mmol) in THF (5 mL) at -70° C. under N$_2$ was added LHMDS (1 M in THF, 1.0 mL). The mixture was warmed to -30° C. and stirred for 30 min. A solution of C$_2$Cl$_6$ (344 mg, 1.40 mmol) in THF (2 mL) was added at -70° C. under N$_2$. The resulting mixture was warmed to room temperature and stirred for 1 h. The reaction was then quenched with water. After removal of the volatiles, the residue was purified by silica gel column chromatography eluting with petroleum ether/ethyl acetate (5/1) to afford the title compound (102 mg, 50%) as a white solid. LC-MS (ESI): m/z=302 (M+H)$^+$.

Step 5—1-((5-chloro-4-nitro-1H-pyrazol-1-yl)methyl)cyclopropanol

To a solution of 5-chloro-4-nitro-1-((1-(tetrahydro-2H-pyran-2-yloxy)cyclopropyl)methyl)-1H-pyrazole (100 mg, 0.330 mmol) in methanol (5 mL) was added 2M HCl/dioxane (1 mL). The mixture was stirred for 2 h. The mixture was concentrated and the residue was purified by reverse phase Combiflash to afford the title compound (66 mg, 90%) as a white solid. LC-MS (ESI): m/z=218 (M+H)$^+$.

Step 6—1-((4-amino-5-chloro-1H-pyrazol-1-yl)methyl)cyclopropanol

To a solution of 1-((5-chloro-4-nitro-1H-pyrazol-1-yl)methyl)cyclopropanol (66 mg, 0.30 mmol) in ethanol (5 mL) was added zinc powder (39 mg, 0.60 mmol) and 1M NH$_4$Cl (1 mL). The mixture was stirred at room temperature for 2 h. The mixture was evaporated and the residue was purified by reverse phase Combiflash to afford the title compound (45 mg, 80%). LC-MS (ESI): m/z=188 (M+H)$^+$.

Examples 1 and 2

N$^2$-(1',5-dimethyl-1'H-1,4'-bipyrazol-4-yl)-N4-methyl-5-(trifluoromethyl)pyrimidine-2,4-diamine and N$^2$-(1',3-dimethyl-1'H-1,4'-bipyrazol-4-yl)-N4-methyl-5-(trifluoromethyl)pyrimidine-2,4-diamine

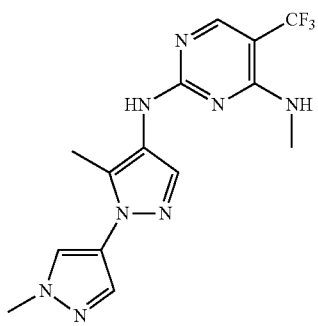

A microwave vial equipped with a magnetic stirrer was charged with the mixture of 1%5-dimethyl-1'H-1,4'-bipyrazol-4-amine and 1',3-dimethyl-1'H-1,4'-bipyrazol-4-amine (50 mg, 0.28 mmol), 2-chloro-N-methyl-5-(trifluoromethyl)pyrimidin-4-amine (60 mg, 0.28 mmol), and t-BuOH (3 mL). The mixture was heated at 100° C. under microwave irradiation for 1 h. After removal of the volatiles, the residue was purified by prep-HPLC to afford N$^2$-(1',5-dimethyl-1'H-1,4'-bipyrazol-4-yl)-N4-methyl-5-(trifluoromethyl)pyrimidine-2,4-diamine (17 mg, 17%) as a white solid and N$^2$-(1',3-dimethyl-1'H-1,4'-bipyrazol-4-yl)-N4-methyl-5-(trifluoromethyl)pyrimidine-2,4-diamine (26 mg, 26%) as a white solid.

N$^2$-(1',5-dimethyl-1'H-1,4'-bipyrazol-4-yl)-N4-methyl-5-(trifluoromethyl)pyrimidine-2,4-diamine $^1$H NMR (500 MHz, DMSO-d$_6$) δ 9.06 (s, 1H), 8.07 (s, 2H), 7.90 (s, 1H), 7.68 (s, 1H), 6.99 (br s, 1H), 3.88 (s, 3H), 2.86 (s, 3H), 2.24 (s, 3H). LC-MS (Method B): m/z=353.3 (M+H)$^+$, 4.42 min, >99.0% purity.

N$^2$-(1',3-dimethyl-1'H-1,4'-bipyrazol-4-yl)-N4-methyl-5-(trifluoromethyl)pyrimidine-2,4-diamine $^1$H NMR (500 MHz, DMSO-d$_6$) δ 9.14 (s, 1H), 8.28 (s, 1H), 8.11 (s, 1H), 8.03 (s, 1H), 7.69 (s, 1H), 7.07 (s, 1H), 3.84 (s, 3H), 2.91 (d, J=4.5 Hz, 3H), 2.21 (s, 3H). LC-MS (Method B): m/z=353.3 (M+H)$^+$, 4.65 min, >99.0% purity.

Compounds made using the above procedure are shown in Table 2 below, together with low resolution mass spectrometry (M+H), proton NMR, and LRRK2 K$_i$ (micromolar) data for selected compounds determined from the assay described below.

TABLE 2

| | Name | Structure | $^1$H NMR | M + H$^+$ | K$_I$ |
|---|---|---|---|---|---|
| 3 | 4-(cyclopropylamino)-2-((5-methyl-1-(tetrahydro-2H-pyran-4-yl)-1H-pyrazol-4-yl)amino)pyrimidine-5-carbonitrile | 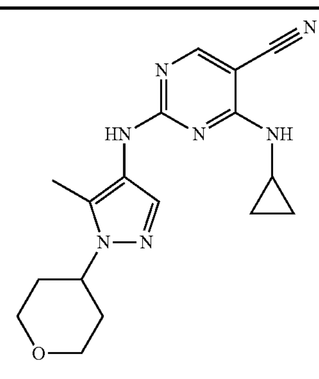 | 1H NMR (500 MHz, CDCl$_3$) δ 8.17 (s, 1H), 8.07-7.60 (m, 1H), 6.92-6.56 (m, 1H), 5.58-5.49 (m, 1H), 4.14-4.25 (m, 3H), 3.58-3.54 (m, 2H), 2.89-2.87 (m, 1H), 2.38-2.30 (m, 5H), 1.88-1.85 (m, 2H), 0.94-0.92 (m, 2H), 0.66-0.65 (m, 2H). | | 0.0073 |

TABLE 2-continued

| Name | Structure | ¹H NMR | M + H⁺ | K_I |
|---|---|---|---|---|
| 4 | 4-(cyclopropylamino)-2-((3-methyl-1-(tetrahydro-2H-pyran-4-yl)-1H-pyrazol-4-yl)amino)pyrimidine-5-carbonitrile | ¹H NMR (500 MHz, CDCl₃) δ 8.26-7.84 (m, 2H), 6.94-6.68 (m, 1H), 5.66-5.47 (m, 1H), 4.30-4.25 (m, 1H), 4.14-4.11 (m, 2H), 3.57-3.52 (m, 2H), 2.89-2.87 (m, 1H), 2.11 (s, 3H), 2.10-1.98 (m, 4H), 0.94-0.92 (m, 2H), 0.74-0.65 (m, 2H) | 340.3 | |
| 5 | 2-((1-(1-cyanopropyl)-5-methyl-1H-pyrazol-4-yl)amino)-4-(cyclopropylamino)pyrimidine-5-carbonitrile | | | |
| 6 | N2-(1-(1-fluoro-2-methylpropan-2-yl)-3-methyl-1H-pyrazol-4-yl)-N4-methyl-5-(trifluoromethyl)pyrimidine-2,4-diamine | ¹H NMR (500 MHz, DMSO-d₆) δ 8.87 (s, 1H), 8.05 (s, 1H), 7.67 (s, 1H), 6.94 (s, 1H), 4.23 (s, 1H), 4.19 (s, 1H), 2.86-2.79 (m, 3H), 2.17 (s, 3H), 1.32 (s, 3H), 1.28 (s, 3H). | 347.1 | |
| 7 | 2-((5-chloro-1-(tetrahydro-2H-pyran-4-yl)-1H-pyrazol-4-yl)amino)-4-(ethylamino)pyrimidine-5-carbonitrile | ¹H NMR (500 MHz, CDCl₃) δ 8.18 (s, 1H), 8.12 (s, 1H), 6.96 (s, 1H), 5.40 (s, 1H), 4.46-4.40 (m, 1H), 4.15-4.12 (m, 2H), 3.57-3.53 (m, 4H), 2.31-2.23 (m, 2H), 1.92-1.63 (m, 2H), 1.28 (t, J = 7.0 Hz, 3H). | 348.1 | 0.0062 |

Example 8

5-Bromo-N²-(1,5-dimethyl-1H-pyrazol-4-yl)-N⁴-methylpyrimidine-2,4-diamine

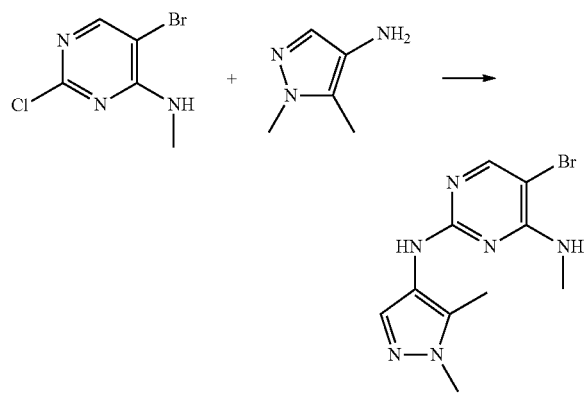

To a mixture of 5-bromo-2-chloro-N-methylpyrimidin-4-amine (0.201 g, 0.903 mmol) and 1,5-dimethyl-1H-pyrazol-4-amine (0.12 g, 1.08 mmol) in 2-methoxyethanol (2 mL) was added TFA (0.070 mL, 0.9 mmol). The reaction was stirred in a sealed tube at 100° C. for 90 minutes. The resulting precipitate was collected by filtration. The isolated solid was further purified by reverse phase HPLC to give 5-bromo-N²-(1,5-dimethyl-1H-pyrazol-4-yl)-N⁴-methylpyrimidine-2,4-diamine (46 mg, 17%). LCMS (Method A): [MH⁺]=297.0 at 2.57 min. ¹H-NMR (DMSO): δ 8.28 (s, 1H), 7.84 (s, 1H), 7.49 (s, 1H), 6.79 (d, J=3.4, 1H), 3.67 (s, 3H), 2.82 (d, J=3.6, 3H), 2.14 (s, 3H). $K_i$=0.017 µM.

Compounds made using the above procedure are shown in Table 3 below, together with low resolution mass spectrometry (M+H), proton NMR, and LRRK2 $K_i$ (micromolar) data for selected compounds determined from the assay described below.

TABLE 3

| | Name | Structure | ¹H NMR | M + H⁺ | $K_i$ |
|---|---|---|---|---|---|
| 9 | 2-methyl-2-(3-methyl-4-((4-(methylamino)-5-(trifluoromethyl)pyrimidin-2-yl)amino)-1H-pyrazol-1-yl)propan-1-ol | 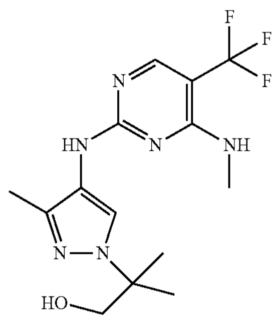 [SMILES: CNc1nc(Nc2cn(C(C)(C)CO)nc2C)ncc1C(F)(F)F] | ¹H NMR (500 MHz, DMSO-d₆) δ 8.98 (s, 1H), 8.11 (s, 1H), 8.08 (s, 1H), 7.02 (s, 1H), 4.91 (t, J = 5.5 Hz, 1H), 3.53 (d, J = 5.5 Hz, 2H), 2.90 (d, J = 4.5 Hz, 3H), 2.15-2.08 (m, 3H), 1.41 (s, 6H). | 345.3 | 0.0048 |
| 10 | 1-((5-chloro-4-((4-(methylamino)-5-(trifluoromethyl)pyrimidin-2-yl)amino)-1H-pyrazol-1-yl)methyl)cyclopropanol | 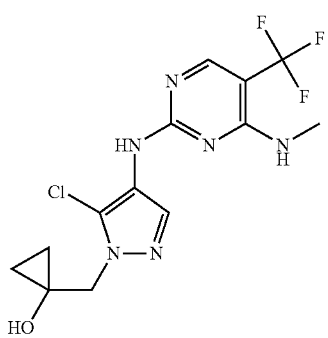 [SMILES: CNc1nc(Nc2cnn(CC3(O)CC3)c2Cl)ncc1C(F)(F)F] | ¹H NMR (500 MHz, CDCl₃) δ 8.18 (s, 1H), 8.14 (s, 1H), 6.80 (s, 1H), 5.26 (s, 1H), 4.22 (s, 2H), 3.92 (s, 1H), 3.09 (d, J = 5.0 Hz, 3H), 0.96-0.93 (m, 2H), 0.75-0.73 (m, 2H). | 363.1 | 0.0050 |

TABLE 3-continued

| Name | Structure | ¹H NMR | M + H⁺ | K$_I$ |
|---|---|---|---|---|
| 11 N2-(3-chloro-1-(2-(4-ethyl-4H-1,2,4-triazol-3-yl)propan-2-yl)-1H-pyrazol-4-yl)-N4-methyl-5-(trifluoromethyl)pyrimidine-2,4-diamine | | ¹H-NMR (500 MHz, CDCl$_3$) δ 8.13 (s, 1H), 7.95 (s, 1H), 7.86 (s, 1H), 7.00 (s , 1H), 5.20 (s, 1H), 3.72 (d, J = 5.0 Hz, 2H), 2.83 (s, 3H), 2.04 (s, 6H), 1.27 (t, J = 7.5 Hz, 3H). | 444.2 | 0.155 |
| 12 N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine | | ¹H NMR (500 MHz, CDCl$_3$) δ 8.16 (s, 1H), 8.13 (s, 1H), 7.98 (s, 1H), 7.01 (s, 1H), 5.24 (s, 1H), 4.18 (d, J = 7.5 Hz, 2H), 3.03 (d, J = 4.5 Hz, 3H), 2.03 (s, 6H), 1.52 (t, J = 7.5 Hz, 3H). | 444.2 | |
| 13 N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine | | | | 0.0029 |

TABLE 3-continued

| Name | Structure | ¹H NMR | M + H⁺ | $K_I$ |
|---|---|---|---|---|
| 14 N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine | | ¹H NMR (500 MHz, CDCl₃) δ 8.13 (s, 2H), 7.98 (s, 1H), 7.03 (s, 1H), 5.21 (s, 1H), 4.21-4.15 (m, 2H), 3.54-3.48 (m, 2H), 2.03 (s, 6H), 1.52 (t, J = 7.0 Hz, 3H), 1.28 (t, J = 7.0 Hz, 3H). | | 0.0011 |
| 15 N4-methyl-N2-(3-methyl-1-(3 methyloxetan-3-yl)-1H-pyrazol-4-yl)-5-(trifluoromethyl)pyrimidine-2,4-diamine | | | | 0.0048 |
| 16 N2-(1-(2-(1,4-dimethyl-1H-imidazol-2-yl)propan-2-yl)-3-methyl-1H-pyrazol-4-yl)-N4-methyl-5-(trifluoromethyl)pyrimidine-2,4-diamine | | ¹H NMR (500 MHz, CDCl₃) δ 8.07 (s, 1H), 7.76 (s, 1H), 6.86 (s, 1H), 6.73 (s, 1H), 5.15 (d, J = 1.5 Hz, 1H), 3.03 (s, 3H), 2.80 (s, 3H), 2.30 (s, 3H), 2.12 (d, J = 1.0 Hz, 3H) 1.98 (s, 6H). | | 0.14 |

TABLE 3-continued

| Name | Structure | $^1$H NMR | M + H$^+$ | K$_I$ |
|---|---|---|---|---|
| 17 N2-(1-(2-(1,4-dimethyl-1H-imidazol-2-yl)propan-2-yl)-3-methyl-1H-pyrazol-4-yl)-N4-methyl-5-(trifluoromethyl)pyrimidine-2,4-diamine | | $^1$H NMR (500 MHz, CDCl$_3$) δ 8.08 (s, 1H), 7.77 (s, 1H), 6.65 (d, J = 3.5 Hz, 1H), 6.49 (s, 1H), 5.15 (s, 1H), 3.08 (s, 3H), 2.83 (s, 3H), 2.28 (s, 3H), 2.20 (s, 3H) 1.98 (s, 6H). | | 0.868 |
| 18 N4-methyl-N2-(3-methyl-1-(2-(5-methyloxazol-2-yl)propan-2-yl)-1H-pyrazol-4-yl)-5-(trifluoromethyl)pyrimidine-2,4-diamine | | $^1$H NMR (500 MHz, CDCl$_3$) δ 8.10 (s, 1H), 7.92 (s, 1H), 6.68 (d, J = 1.5 Hz, 1H) 6.61 (d, J = 7.5 Hz, 1H), 5.18 (t, J = 3.0 Hz, 1H), 2.99 (d, J = 4.5 Hz, 3H), 2.28 (t, J = 1.0 Hz, 6H), 2.00 (s, 6H). | | 0.00382 |
| 19 N4-ethyl-N2-(3-methyl-1-(3-methyloxetan-3-yl)-1H-pyrazol-4-yl)-5-(trifluoromethyl)pyrimidine-2,4-diamine | | $^1$H NMR (500 MHz, CDCl$_3$) δ 8.15 (s, 1H), 8.01 (s, 1H), 6.86-6.42 (m, 1H), 5.18 (s, 1H), 5.17 (d, J = 6.0 Hz, 2H), 4.64 (d, J = 6.0 Hz, 2H), 3.57-3.54 (m, 2H), 2.30 (s, 3H), 1.94 (s, 3H), 1.30 (t, J = 7.0 Hz, 3H) | | 0.000975 |
| 20 N4-ethyl-N2-(1-((2-methoxyethyl)sulfonyl)-3-methyl-1H-pyrazol-4-yl)-5-(trifluoromethyl)pyrimidine-2,4-diamine | | | | 0.00096 |

TABLE 3-continued

| Name | Structure | ¹H NMR | M + H⁺ | K$_I$ |
|---|---|---|---|---|
| 21 N2-(1-((2-methoxyethyl)sulfonyl)-3-methyl-1H-pyrazol-4-yl)-N4-methyl-5-(trifluoromethyl)pyrimidine-2,4-diamine | | | | 0.00185 |
| 22 N2-(1-((2-methoxyethyl)sulfonyl)-5-methyl-1H-pyrazol-4-yl)-N4-methyl-5-(trifluoromethyl)pyrimidine-2,4-diamine | | | | 0.00646 |
| 23 N2-(5-chloro-1-(2-(4-methyl-4H-1,2,4-triazol-3-yl)propan-2-yl)-1H-pyrazol-4-yl)-N4-ethyl-5-(trifluoromethyl)pyrimidine-2,4-diamine | | | | 0.0011 |
| 24 N4-methyl-N2-(5-methyl-1-(2-(1-methyl-1H-pyrazol-3-yl)propyl)-1H-pyrazol-4-yl)-5-(trifluoromethyl)pyrimidine-2,4-diamine | | ¹H NMR (500 MHz, CDCl₃) δ 8.09 (s, 1H), 7.49 (s, 1H), 7.40 (s, 1H), 6.59 (s, 1H), 6.11 (s, 1H), 5.16 (s, 1H), 4.18-4.14 (m, 1H), 4.06-4.02 (m, 1H), 3.56 (s, 3H), 3.49-3.45 (m, 1H), 2.96 (d, J = 5.0 Hz, 3H), 2.25 (s, 3H), 1.29 (d, J = 6.5 Hz, 3H). | 395.3 | 0.0166 |

TABLE 3-continued

| Name | Structure | ¹H NMR | M + H⁺ | K$_I$ |
|---|---|---|---|---|
| 25 N4-methyl-N2-(5-methyl-1-(2-(1-methyl-1H-pyrazol-3-yl)propyl)-1H-pyrazol-4-yl)-5-(trifluoromethyl)pyrimidine-2,4-diamine | | ¹H NMR (500 MHz, CDCl$_3$) δ 8.08 (s, 1H), 7.81 (s, 1H), 7.40 (s, 1H), 6.14 (s, 1H), 5.20 (s, 1H), 4.20-4.17 (m, 1H), 4.01-3.97 (m, 1H), 3.54-3.50 (m, 1H), 3.44 (s, 3H), 3.00 (d, J = 5.0 Hz, 3H), 1.81 (s, 3H), 1.35 (d, J = 7.0 Hz, 3H). | 395.3 | 0.108 |
| 26 N4-methyl-N2-(3-methyl-1-(2-(pyrimidin-2-yl)propan-2-yl)-1H-pyrazol-4-yl)-5-(trifluoromethyl)pyrimidine-2,4-diamine | | %). ¹H NMR (500 MHz, CDCl$_3$) δ 8.71 (d, J = 5.0 Hz, 2H), 8.12 (d, J = 21.5 Hz, 2H), 7.17-7.13 (m, 1H), 5.22 (s, 1H), 3.03 (d, J = 4.5 Hz, 3H), 2.24 (s, 3H), 2.05 (s, 6H). | 393.3 | 0.0043 |
| 27 N2-(3-chloro-1-(2-(5-methyl-1,3,4-oxadiazol-2-yl)propan-2-yl)-1H-pyrazol-4-yl)-N4-ethyl-5-(trifluoromethyl)pyrimidine-2,4-diamine | | ¹H NMR (500 MHz, CDCl$_3$) δ 8.14 (s, 2H), 6.80 (br s, 1H), 5.17 (br s, 1H), 3.53-3.47 (m, 2H), 2.51 (s, 3H), 2.07 (s, 6H), 1.60 (s, 3H) | 431.1 | 0.0037 |
| 28 N⁴-ethyl-N²-(3-methyl-1-(2-(5-methyl-1,3,4-oxadiazol-2-yl)propan-2-yl)-1H-pyrazol-4-yl)-5-(trifluoromethyl)pyrimidine-2,4-diamine | | . ¹H NMR (500 MHz, CDCl$_3$) δ 8.23 (s, 1H), 8.02 (s, 1H), 6.95 (s, 1H), 5.19 (s, 1H), 3.53-3.46 (m, 2H), 2.49 (s, 3H), 2.25 (s, 3H), 2.06 (s, 6H), 1.28 (d, J = 7.3 Hz, 3H) | | |

TABLE 3-continued

| Name | Structure | $^1$H NMR | M + H$^+$ | K$_I$ |
|---|---|---|---|---|
| 29 N4-ethyl-N2-(1-(2-(5-ethyl-1,3,4-oxadiazol-2-yl)propan-2-yl)-3-methyl-1H-pyrazol-4-yl)-5-(trifluoromethyl)pyrimidine-2,4-diamine | | $^1$H NMR (500 MHz, CDCl$_3$) δ 8.11 (s, 1H), 8.01 (s, 1H), 6.64 (s, 1H), 5.15 (s, 1H), 3.52-3.46 (m, 2H), 2.85-2.80 (m, 2H), 2.25 (s, 3H), 2.06 (s, 6H), 1.34 (d, J = 7.5 Hz, 3H), 1.29 (t, J = 7.3 Hz, 3H). | | 0.0065 |
| 30 N4-ethyl-N2-(1-(2-(1-isopropyl-1H-1,2,4-triazol-3-yl)propan-2-yl)-3-methyl-1H-pyrazol-4-yl)-5-(trifluoromethyl)pyrimidine-2,4-diamine | | $^1$H NMR (500 MHz, DMSO-d$_6$) δ 8.95 (s, 1H), 8.47 (s, 1H), 8.07 (s, 1H), 7.85 (s, 1H), 7.04 (s, 1H), 4.54 (t, J = 6.5 Hz, 1H), 3.33 (s, 2H), 2.14 (s, 3H), 1.86 (s, 6H), 1.43 (s, 3H), 1.42 (s, 3H), 1.08-1.13 (m, 3H). | 438.3 | 0.0006 |
| 31 N2-(3-chloro-1-(2-(4-methyl-4H-1,2,4-triazol-3-yl)propan-2-yl)-1H-pyrazol-4-yl)-N4-ethyl-5-(trifluoromethyl)pyrimidine-2,4-diamine | | $^1$H NMR (500 MHz, CDCl$_3$) δ 8.13 (s, 1H), 7.92 (s, 1H), 7.82 (s, 1H), 7.00 (s, 1H), 5.16 (s, 1H), 3.43 (s, 3H), 3.28 (s, 2H), 2.04 (s, 6H), 1.21 (t, J = 6.0 Hz, 3H) | | 0.0425 |

TABLE 3-continued

| Name | Structure | $^1$H NMR | M + H$^+$ | K$_I$ |
|---|---|---|---|---|
| 32 N2-(3-chloro-1-(2-(1-methyl-1H-1,2,4-triazol-3-yl)propan-2-yl)-1H-pyrazol-4-yl)-N4-ethyl-5-(trifluoromethyl)pyrimidine-2,4-diamine | | $^1$H NMR (500 MHz, CDCl$_3$) δ 8.15 (s, 1H), 8.12 (s, 1H), 7.95 (s, 1H), 7.01 (s, 1H), 5.19 (s, 1H), 3.89 (s, 3H), 3.52 (m, 2H), 2.03 (s, 6H), 1.28 (t, J = 7.0 Hz, 3H). | | 0.0005 |
| 33 N4-methyl-N2-(5-methyl-1-(2-(1-methyl-1H-pyrazol-3-yl)ethyl)-1H-pyrazol-4-yl)-5-(trifluoromethyl)pyrimidine-2,4-diamine | | $^1$H NMR (500 MHz, DMSO-d$_6$) δ 8.86 (s, 1H), 8.05 (s, 1H), 7.69 (s, 1H), 7.54 (d, J = 1.5 Hz, 1H), 6.93 (s, 1H), 5.97 (s, 1H), 4.19 (t, J = 7.5 Hz, 2H), 3.76 (s, 3H), 2.95 (t, J = 7.5 Hz, 2H), 2.82 (s, 3H), 2.12 (s, 3H). | | 0.0020 |
| 34 N4-ethyl-N2-(3-methyl-1-(2-(1-methyl-1H-pyrazol-3-yl)propan-2-yl)-1H-pyrazol-4-yl)-5-(trifluoromethyl)pyrimidine-2,4-diamine | | | | 0.0217 |

TABLE 3-continued

| Name | Structure | ¹H NMR | M + H⁺ | $K_I$ |
|---|---|---|---|---|
| 35 N4-ethyl-N2-(3-methyl-1-(2-(1-methyl-1H-pyrazol-5-yl)propan-2-yl)-1H-pyrazol-4-yl)-5-(trifluoromethyl)pyrimidine-2,4-diamine | | | | 0.0003 |
| 36 N4-methyl-N2-(3-methyl-1-(2-(1-methyl-1H-pyrazol-3-yl)ethyl)-1H-pyrazol-4-yl)-5-(trifluoromethyl)pyrimidine-2,4-diamine | | ¹H NMR (500 MHz, DMSO-d₆) δ 8.91 (s, 1H), 8.07 (s, 1H), 7.86 (s, 1H), 7.54 (s, 1H), 6.98 (s, 1H), 5.99 (s, 1H), 4.22 (s, 2H), 3.75 (s, 3H), 2.99 (t, J = 7.5 Hz, 2H), 2.85 (s, 3H), 2.13 (s, 3H) | | 0.0037 |
| 37 N2-(1-(3-fluorotetrahydro-2H-pyran-4-yl)-3-methyl-1H-pyrazol-4-yl)-N4-methyl-5-(trifluoromethyl)pyrimidine-2,4-diamine | | ¹H NMR (500 MHz, CDCl₃) δ 8.08 (s, 1H), 7.89-7.83 (m, 1H), 6.66-6.61 (m, 1H), 5.13 (s 1H), 4.96-4.81 (m, 1H), 4.28-4.08 (m, 3H), 3.54-3.37 (m, 2H), 3.00-2.99 (d, J = 4.5 Hz, 3H), 2.59-2.50 (m, 1H), 2.25 (s, 3H), 2.21-2.04 (m, 1H) | | 0.0006 |
| 38 N2-(1-(3-fluorotetrahydro-2H-pyran-4-yl)-3-methyl-1H-pyrazol-4-yl)-N4-methyl-5-(trifluoromethyl)pyrimidine-2,4-diamine | | | | |

TABLE 3-continued

| Name | Structure | ¹H NMR | M + H⁺ | K$_I$ |
|---|---|---|---|---|
| 39 N2-(1-(3-fluorotetrahydro-2H-pyran-4-yl)-5-methyl-1H-pyrazol-4-yl)-N4-methyl-5-(trifluoromethyl)pyrimidine-2,4-diamine | | | | 0.0028 |
| 40 N2-(1-((3R)-3-fluorotetrahydro-2H-pyran-4-yl)-5-methyl-1H-pyrazol-4-yl)-N4-methyl-5-(trifluoromethyl)pyrimidine-2,4-diamine | | | | 0.0006 |
| 41 3-methyl-3-(3-methyl-4-((4-(methylamino)-5-(trifluoromethyl)pyrimidin-2-yl)amino)-1H-pyrazol-1-yl)butanenitrile | | | | 0.0128 |
| 42 2-((3-methyl-4-((4-(methylamino)-5-(trifluoromethyl)pyrimidin-2-yl)amino)-1H-pyrazol-1-yl)methyl)butanenitrile | | ¹H NMR (500 MHz, CD$_3$OD) δ 8.04 (s, 2H), 4.34-4.31 (m, 2H), 3.24-3.19 (m, 1H), 2.99 (s, 3H), 2.24 (s, 3H), 1.74-1.60 (m, 2H), 1.14 (t, J = 7.5 Hz, 3H). | 354.3 | 0.0041 |

Example 43

3-methyl-3-(3-methyl-4-(4-(methylamino)-5-(trifluoromethyl)pyrimidin-2-ylamino)-1H-pyrazol-1-yl)butanenitrile

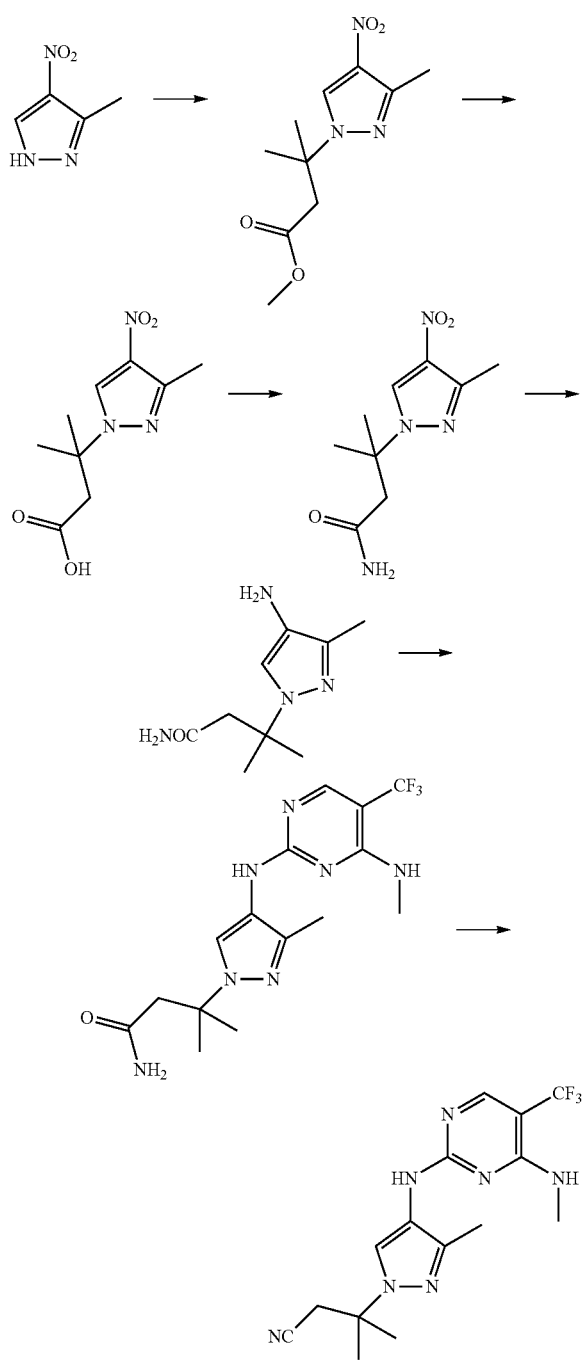

Step 1—methyl 3-methyl-3-(3-methyl-4-nitro-1H-pyrazol-1-yl)butanoate

A solution of 3-methyl-4-nitro-1H-pyrazole (1.00 g, 7.87 mmol), methyl 3-methylbut-2-enoate (2.20 g, 18.9 mmol), and DBU (3.10 g, 20.5 mmol) in DMF (5.0 mL) was stirred overnight. The mixture was purified by reverse phase Combiflash to afford the title compound (130 mg, 7%) as yellow oil. LC-MS (ESI): m/z=242 (M+H)$^+$.

Step 2—3-methyl-3-(3-methyl-4-nitro-1H-pyrazol-1-yl)butanoic acid

To a solution of methyl 3-methyl-3-(3-methyl-4-nitro-1H-pyrazol-1-yl)butanoate (508 mg, 2.10 mmol) in EtOH (10 mL) and H$_2$O (10 mL) was added LiOH (265 mg, 6.30 mmol). The reaction mixture was stirred for 12 h. The mixture was acidified to pH around 5. The resulting mixture was extracted with EtOAc, washed with brine, and dried over Na$_2$SO$_4$. Removal of the solvents afforded the title compound (450 mg, 94%). LC-MS (ESI): m/z=228.1 (M+H)$^+$.

Step 3—3-methyl-3-(3-methyl-4-nitro-1H-pyrazol-1-yl)butanamide

To a solution of 3-methyl-3-(3-methyl-4-nitro-1H-pyrazol-1-yl)butanoic acid (450 mg, 1.98 mmol) in SOCl$_2$ (5.0 mL) was added a catalytic amount of DMF. After being stirred for 3 h, NH$_3$H$_2$O (173 mg, 4.95 mmol) was added. The mixture was further stirred for 3 h. After removal of volatiles, the residue was extracted with EtOAc, washed with brine, dried over Na$_2$SO$_4$, and concentrated. The residue was purified by prep-TLC eluting with ethyl acetate/petroleum ether (1/3 to 1/1) to afford the title compound (372 mg, 83%). LC-MS (ESI): m/z=227.1 (M+H)$^+$.

Step 4—3-(4-amino-3-methyl-1H-pyrazol-1-yl)-3-methylbutanamide

A mixture of 3-methyl-3-(3-methyl-4-nitro-1H-pyrazol-1-yl)butanamide (372 mg, 1.64 mmol) and 10% Pd/C (20 mg) in MeOH (10 mL) was stirred under H$_2$ atmosphere for 4 h. After filtering off the insoluble material, the filtrate was concentrated to give the title compound (306 mg, 95%). LC-MS (ESI): m/z=197.1 (M+H)$^+$.

Step 5—3-methyl-3-(3-methyl-4-(4-(methylamino)-5-(trifluoromethyl)pyrimidin-2-ylamino)-1H-pyrazol-1-yl)butanamide To a solution of 3-(4-amino-3-methyl-1H-pyrazol-1-yl)-3-methylbutanamide (306 mg, 1.56 mmol) in t-BuOH (2 mL) was added 2-chloro-N-methyl-5-(trifluoromethyl)pyrimidin-4-amine (329 mg, 1.56 mmol). The reaction mixture was heated at 100° C. under microwave irradiation for 1 h. After concentration, the residue was purified by prep-TLC eluting with ethyl acetate/petroleum ether (1/3 to 1/1) to afford the title compound (347 mg, 60%). LC-MS (ESI): m/z=372.2 (M+H)$^+$.

Step 6—3-methyl-3-(3-methyl-4-(4-(methylamino)-5-(trifluoromethyl)pyrimidin-2-ylamino)-1H-pyrazol-1-yl)butanenitrile To a solution of 3-methyl-3-(3-methyl-4-(4-(methylamino)-5-(trifluoromethyl)pyrimidin-2-ylamino)-1H-pyrazol-1-yl)butanamide (100 mg, 0.270 mmol) in DCM (10 mL) was added TFA (2 mL) dropwise at 0° C. The reaction mixture was stirred at 0° C. for 1 h. After being quenched by ice water, the mixture was extracted with EtOAc, washed with brine, and dried over Na$_2$SO$_4$, and concentrated. The residue was purified by prep-HPLC to give the title compound (45 mg, 47%). $^1$H NMR (500 MHz, CDCl$_3$) δ 8.12-8.03 (m, 2H), 6.69 (s, 1H), 5.21 (s, 1H), 3.11 (s, 3H), 2.98 (s, 2H), 2.25 (s, 3H), 1.76 (s, 6H). LC-MS (Method B): m/z=354.3 (M+H)$^+$, 5.19 min, >99.0% purity.

Compounds made using the above procedure are shown in Table 10 below, together with low resolution mass spectrometry (M+H), proton NMR, and LRRK2 $K_i$ (micromolar) data for selected compounds determined from the assay described below.

TABLE 4

| Name | Structure | ¹H NMR | M + H⁺ | $K_I$ |
|---|---|---|---|---|
| 44 2-(5-((4-(ethylamino)-5-(trifluoromethyl)pyrimidin-2-yl)amino)-1-methyl-1H-pyrazol-3-yl)-2-methylpropanenitrile | | | | 0.0007 |
| 45 2-methyl-2-(1-methyl-5-((4-(methylamino)-5-(trifluoromethyl)pyrimidin-2-yl)amino)-1H-pyrazol-3-yl)propanenitrile | | ¹H NMR (500 MHz, DMSO-d₆) δ 9.56 (s, 1H), 8.17 (s, 1H), 7.20 (d, J = 4.0 Hz, 1H), 6.37 (s, 1H), 3.66 (s, 3H), 2.87 (d, J = 3.5 Hz, 3H), 1.63 (s, 6H). | | 0.0086 |
| 46 2-((1-(2-cyanopropan-2-yl)-3-methyl-1H-pyrazol-4-yl)amino)-4-(cyclopropylamino)pyrimidine-5-carbonitrile | | | | 0.003 |
| 47 2-((1-(2-cyanopropan-2-yl)-3-methyl-1H-pyrazol-4-yl)amino)-4-(cyclopropylamino)pyrimidine-5-carbonitrile | | ¹H NMR (500 MHz, CDCl₃) δ 8.48 (s, 1H), 8.18 (s, 1H), 6.86 (s, 1H), 5.36 (s, 1H), 2.93 (s, 1H), 2.28 (s, 3H), 2.00-1.96 (m, 1.02-1.00 (m, 2H), 0.68-0.65 (m, 2H). | | |

TABLE 4-continued

| Name | Structure | ¹H NMR | M + H⁺ | K$_I$ |
|---|---|---|---|---|
| 48 2-((1-(2-cyanopropan-2-yl)-3-methyl-1H-pyrazol-4-yl)amino)-4-(ethylamino)pyrimidine-5-carbonitrile | | | | |
| 49 2-methyl-2-(3-methyl-4-((4-(methylamino)-5-(trifluoromethyl)pyrimidin-2-yl)amino)-1H-pyrazol-1-yl)butanenitrile | | ¹H NMR (500 MHz, DMSO-d₆) δ 9.17 (s, 1H), 8.27 (s, 1H), 8.12 (s, 1H), 7.10 (s, 1H), 2.89 (d, J = 4.5 Hz, 3H), 2.24-2.14 (m, 5H), 1.87 (s, 3H), 0.87 (t, J = 7.5 Hz, 3H). | 354.3 | |
| 50 5-((4-(ethylamino)-5-(trifluoromethyl)pyrimidin-2-yl)amino)-1-methyl-1H-pyrazole-3-carbonitrile | | | | 0.0245 |

Example 51

In Vitro LRRK2 Lanthascreen Binding Assay

This assay was used to determine a compound's potency in inhibiting activity of LRRK2 by determining, Ki$_{app}$, IC$_{50}$, or percent inhibition values. In 384 well proxiplates F black, shallow well plates LRRK2, Eu-anti-GST-antibody, Alexa Fluor® Kinase tracer 236 and test compound were incubated together.

Binding of the Alexa Fluor® "tracer" to a kinase is detected by addition of a Eu-labeled anti-GST antibody. Binding of the tracer and antibody to a kinase results in a high degree of FRET, whereas displacement of the tracer with a kinase inhibitor results in a loss of FRET.

Assay conditions and materials used were as follows:
Final Assay Conditions:

| | |
|---|---|
| GST-LRRK2 G2019S | 10 nM |
| Eu-anti-GST-antibody | 2 nM |
| Kinase tracer 236 | 8.5 nM |
| Kinase reaction time: | 1 hour |
| Temperature: | ambient |
| Total volume: | 15 µl |
| DMSO | 1% |

Materials:

| | |
|---|---|
| 384 well proxiplates F black shallow well Perkin Elmer | cat# 6008260 |
| Kinase: LRRK2 G2019S, | Invitrogen cat # PV4882(LOT 567054A). |
| Eu-labeled anti-GST antibody | Invitrogen cat # PV5594 |
| Alexa Fluor ® Kinase tracer 236 | Invitrogen cat #PV5592 |
| TRIS-HCl | Sigma cat # T3253 |
| EGTA | Sigma cat # E3889 |
| Brij-35: | Sigma cat # B4184(30% w/v) |
| DMSO: | Sigma cat # D8418 |
| MgCl₂ | Sigma cat # M9272 |

Reaction Buffer: H₂O/50 mM Tris, pH 7.4/10 mM MgCl₂/1 mM EGTA/0.01% Brij 35

Compound Plate Preparation:

Serially dilute test compounds (10 mM stock) 1:3.16 (20 ul+43.2 ul) in 100% DMSO. 12 pt curve. Dilute each concentration 1:33.3 (3 ul+97 ul) in reaction buffer. Stamp 5 ul to assay plate. Final top test concentration 100 uM Total and Blank Preparation:

In Reaction Buffer, 5 ul of DMSO (3%) was added to total and blank wells and 5 ul of Eu-labeled anti-GST antibody (6 nM) was added to blank wells. Add 5 ul LRRK2 (30 nM)/Eu-labeled anti-GST antibody (6 nM) mix to compound and total wells.

Assay Procedure:

Add 5 ul kinase tracer (25.5 nM) to all wells. Incubate plates at room temperature for 1 hour on a plate shaker (gentle shaking). Read on Perkin Elmer EnVision reader HTRF protocol Data Handling:

Calculate ratio: (665/620)*10000. Subtract mean background values from all data points. Calculate % of control for each test value. Plot % of control vs Compound concentration. Calculate Ki Value (xlfit curve fitting-Morrison equation). Results expressed as a Ki in μM. Equation for Ki:

$$Y=V0*(1-((x+Ki*(1+S/Km)+Et)/(2*Et)-(((x+Ki*(1+S/Km)+Et)^2-(4*Et*x))^0.5)/(2*Et)))$$

Where Et=4 nM
kd (Tracer)=8.5 nM
Tracer concentration (S)=8.5 nM

Example 52

In Vitro LRRK2 Assay

This assay was used to determine a compound's potency in inhibiting activity of LRRK2 by determining, $Ki_{app}$, $IC_{50}$, or percent inhibition values. In a polypropylene plate, LRRK2, fluorescently-labeled peptide substrate, ATP and test compound were incubated together. Using a LabChip 3000 (Caliper Life Sciences), after the reaction the substrate was separated by capillary electrophoresis into two populations: phosphorylated and unphosphorylated. The relative amounts of each were quantitated by fluorescence intensity. LRRK2 Ki was determined according to the equation:

$$Y=V0*(1-((x+Ki*(1+S/Km)+Et)/(2*Et)-(((x+Ki*(1+S/Km)+Et)^2-(4*Et*x))^0.5)/(2*Et))).$$

Ki values in Table 4 and elsewhere herein are shown in μM. Assay conditions and materials used were as follows:
Final Assay Conditions:

| | |
|---|---|
| LRRK2 G2019S in 5 mM MgCl$_2$: | 5.2 nM (Invitrogen lot # 567054A) |
| LRRK2 G2019S in 1 mM MnCl$_2$: | 11 nM (Invitrogen lot # 567054A) |
| LRRK2 Wild type in 5 mM MgCl$_2$: | 15 nM (Invitrogen lot # 500607F) |
| LRRK2 I2020T in 5 mM MgCl$_2$: | 25 nM (Invitrogen lot # 43594) |
| Substrate: | 1 μM |
| ATP: | 130 μM |
| Kinase reaction time: | 2 hours |
| Temperature: | ambient |
| Total volume: | 20 μl |

$ATP^{app}$ Kms:

| | |
|---|---|
| G2019S in 5 mM MgCl$_2$: | 130 μM |
| G2019S in 1 mM MnCl$_2$: | 1 μM |
| Wild type in 5 mM MgCl$_2$: | 80 μM |
| I2020T in 5 mM MgCl$_2$: | 14 μM |

Materials:

| | |
|---|---|
| Solid Support: | Black 50 μL volume polypropylene 384 well plate (MatriCal cat # MP101-1-PP) |
| Kinase: | LRRK2 G2019S (Invitrogen cat # PV4882). LRRK2 Wild type (Invitrogen cat # PV4874). |
| Substrate: | 5FAM-GAGRLGRDKYKTLRQIRQ-CONH$_2$ |
| Non-binding plate: | 384 well clear V-bottom polypropylene plates (Greiner cat # 781280). |
| ATP: | 10 mM ATP (Cell Signaling cat # 9804). |
| Triton X-100: | Triton X-100. |
| Brij-35: | Brij-35 (Pierce cat # 20150). |
| Coating Reagent #3: | Coating Reagent #3 (Caliper). |
| DMSO: | DMSO (Sigma cat # 34869-100ML). |
| Complete Reaction Buffer: | H$_2$O/25 mM Tris, pH 8.0/5 mM MgCl$_2$/2 mM DTT/0.01% Triton X-100. |
| Stop Solution: | H$_2$O/100 mM HEPES, pH 7.2/0.015% Brij-35/0.2% Coating Reagent #3/20 mM EDTA. |
| Separation Buffer: | H$_2$O/100 mM HEPES, pH 7.2/0.015% Brij-35/0.1% Coating Reagent #3/1:200 Coating Reagent #8/10 mM EDTA/5% DMSO. |

Compound Plate Preparation:

For serial dilutions, 34.6 μl DMSO was added to columns 3-24. For the assay controls, 37.5 μl DMSO was added to columns 1 and 2 of rows A and P. a,d and 50 μl 25 μM G-028831 (Staurosporine) was added to columns 1 and 2, row B. For the samples: to start at 100 μM, 37.5 μl DMSO was to columns 1 and 2, then 12.5 μl 10 mM compound; to start at 10 μM, 78 μl DMSO was added to columns 1 & 2, then 2 μl 10 mM compound; and to start at 1 μM, 25 μM compound (2 μl 10 mM cmpd+798 μl DMSO) was added to empty columns 1 and 2. A Precision instrument was used to perform 1:3.16 serial dilutions ("PLK_BM_serial_halflog").

ATP Preparation:

ATP was diluted to 282.1 μM in Complete Kinase Buffer (final concentration was 130 μm).

Total and Blank Preparation:

In Complete Reaction Buffer, substrate was diluted to 4 μM. Equal volumes of Complete Reaction Buffer and 4 μM substrate were combined to obtain the blank. Equal volumes of Complete Reaction Buffer and 4 μM substrate were combined and to the combined solution was added 2× final LRRK2 concentration.

Assay Procedure:

To a 50 μl polypropylene plate, 5 μl/well buffer/substrate was added by hand to Blank wells. A Biomek FX was used to start the kinase reaction ("PLK SAR 23 ATP"). The following were added to the appropriate wells:

2 μl compound+23 μl ATP;
5 μl/well compound/ATP in Assay Plate;
5 μl/well kinase/substrate in Assay Plate;

The plate was incubated for 2 hours in the dark. Biomek FX was used to stop the kinase reaction ("PLK Stop"), and 10 μl/well Stop solution was added to the Assay Plate. Results were read on the LabChip 3000.

Lab Chip 3000 Protocol:

The LabChip 3000 was run using the job "LRRK2 IC50" with the following job settings:

| | |
|---|---|
| Pressure: | −1.4 psi |
| Downstream voltage: | −500 V |
| Upstream voltage: | −2350 V |
| Post sample buffer sip time: | 75 seconds |
| Post dye buffer sip time: | 75 seconds |
| Final delay time: | 200 seconds |

Example 53

Parkinson's Disease Mouse Model

Parkinson's disease can be replicated in mice and in primates by administration of 1-methyl-4-phenyl tetrahydropyridine (MPTP), a selective nigrostriatal dopaminergic neurotoxin that produces a loss of striatal dopamine (DA) nerve terminal markers. Compounds of the invention may be evaluated for effectiveness in treatment of Parkinson's disease using MPTP induced neurodegeneration following generally the protocol described by Saporito et al., *J. Pharmacology* (1999) Vol. 288, pp. 421-427.

Briefly, MPTP is dissolved in PBS at concentrations of 2-4 mg/ml, and mice (male C57 weighing 20-25 g) are given a subcutaneous injection of 20 to 40 mg/kg. Compounds of the invention are solubilized with polyethylene glycol hydroxystearate and dissolved in PBS. Mice are administered 10 ml/kg of compound solution by subcutaneous injection 4 to 6 h before MPTP administration, and then daily for 7 days. On the day of the last injection, mice are sacrificed and the midbrain blocked and postfixed in paraformaldehyde. Striata are dissected free, weighed, and stored at −70° C.

The striata thus collected are evaluated for content of dopamine and its metabolites dihydroxyphenylacetic acid and homovanillic acid, by HPLC with electrochemical detection as described by Sonsalla et al., *J. Pharmacol. Exp. Ther.* (1987) Vol. 242, pp. 850-857. The striata may also be evaluated using the tyrosine hydroxylase assay of Okunu et al., *Anal Biochem* (1987) Vol. 129, pp. 405-411 by measuring $^{14}CO_2$ evolution associated with tyrosine hydroxylase-mediated conversion of labeled tyrosine to L-dopa. The striata may further be evaluated using the Monoamine oxidase-B assay as described by White et al., *Life Sci.* (1984), Vol. 35, pp. 827-833, and by monitoring dopamine uptake as described by Saporito et al., (1992) Vol. 260, pp. 1400-1409.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound selected from:
$N^2$-(1',5-dimethyl-1'H-1,4'-bipyrazol-4-yl)-N4-methyl-5-(trifluoromethyl)pyrimidine-2,4-diamine;
$N^2$-(1',3-dimethyl-1'H-1,4'-bipyrazol-4-yl)-N4-methyl-5-(trifluoromethyl)pyrimidine-2,4-diamine;
4-(cyclopropylamino)-2-((5-methyl-1-(tetrahydro-2H-pyran-4-yl)-1H-pyrazol-4-yl)amino)pyrimidine-5-carbonitrile;
4-(cyclopropylamino)-2-((3-methyl-1-(tetrahydro-2H-pyran-4-yl)-1H-pyrazol-4-yl)amino)pyrimidine-5-carbonitrile;
2-((1-(1-cyanopropyl)-5-methyl-1H-pyrazol-4-yl)amino)-4-(cyclopropylamino)pyrimidine-5-carbonitrile;
N2-(1-(1-fluoro-2-methylpropan-2-yl)-3-methyl-1H-pyrazol-4-yl)-N4-methyl-5-(trifluoromethyl)pyrimidine-2,4-diamine;
2-((5-chloro-1-(tetrahydro-2H-pyran-4-yl)-1H-pyrazol-4-yl)amino)-4-(ethylamino)pyrimidine-5-carbonitrile;
5-bromo-$N^2$-(1,5-dimethyl-1H-pyrazol-4-yl)-$N^4$-methylpyrimidine-2,4-diamine;
2-methyl-2-(3-methyl-4-((4-(methylamino)-5-(trifluoromethyl)pyrimidin-2-yl)amino)-1H-pyrazol-1-yl)propan-1-ol;
1-((5-chloro-4-((4-(methylamino)-5-(trifluoromethyl)pyrimidin-2-yl)amino)-1H-pyrazol-1-yl)methyl)cyclopropanol;
N2-(3-chloro-1-(2-(4-ethyl-4H-1,2,4-triazol-3-yl)propan-2-yl)-1H-pyrazol-4-yl)-N4-methyl-5-(trifluoromethyl)pyrimidine-2,4-diamine;
N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;
N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;
N2-(3-chloro-1-(2-(1-ethyl-1H-1,2,4-triazol-3-yl)propan-2-yl)-1H-pyrazol-4-yl)-N4-methyl-5-(trifluoromethyl)pyrimidine-2,4-diamine;
N4-methyl-N2-(3-methyl-1-(3-methyloxetan-3-yl)-1H-pyrazol-4-yl)-5-(trifluoromethyl)pyrimidine-2,4-diamine;
N2-(1-(2-(1,4-dimethyl-1H-imidazol-2-yl)propan-2-yl)-3-methyl-1H-pyrazol-4-yl)-N4-methyl-5-(trifluoromethyl)pyrimidine-2,4-diamine;
N2-(1-(2-(1,4-dimethyl-1H-imidazol-2-yl)propan-2-yl)-3-methyl-1H-pyrazol-4-yl)-N4-methyl-5-(trifluoromethyl)pyrimidine-2,4-diamine;
N4-methyl-N2-(3-methyl-1-(2-(5-methyloxazol-2-yl)propan-2-yl)-1H-pyrazol-4-yl)-5-(trifluoromethyl)pyrimidine-2,4-diamine;
N4-ethyl-N2-(3-methyl-1-(3-methyloxetan-3-yl)-1H-pyrazol-4-yl)-5-(trifluoromethyl)pyrimidine-2,4-diamine;
N4-ethyl-N2-(1-((2-methoxyethyl)sulfonyl)-3-methyl-1H-pyrazol-4-yl)-5-(trifluoromethyl)pyrimidine-2,4-diamine;
N2-(1-((2-methoxyethyl)sulfonyl)-3-methyl-1H-pyrazol-4-yl)-N4-methyl-5-(trifluoromethyl)pyrimidine-2,4-diamine;
N2-(1-((2-methoxyethyl)sulfonyl)-5-methyl-1H-pyrazol-4-yl)-N4-methyl-5-(trifluoromethyl)pyrimidine-2,4-diamine;
N2-(5-chloro-1-(2-(4-methyl-4H-1,2,4-triazol-3-yl)propan-2-yl)-1H-pyrazol-4-yl)-N4-ethyl-5-(trifluoromethyl)pyrimidine-2,4-diamine;
N4-methyl-N2-(5-methyl-1-(2-(1-methyl-1H-pyrazol-3-yl)propyl)-1H-pyrazol-4-yl)-5-(trifluoromethyl)pyrimidine-2,4-diamine;
N4-methyl-N2-(5-methyl-1-(2-(1-methyl-1H-pyrazol-3-yl)propyl)-1H-pyrazol-4-yl)-5-(trifluoromethyl)pyrimidine-2,4-diamine;
N4-methyl-N2-(3-methyl-1-(2-(pyrimidin-2-yl)propan-2-yl)-1H-pyrazol-4-yl)-5-(trifluoromethyl)pyrimidine-2,4-diamine;
N2-(3-chloro-1-(2-(5-methyl-1,3,4-oxadiazol-2-yl)propan-2-yl)-1H-pyrazol-4-yl)-N4-ethyl-5-(trifluoromethyl)pyrimidine-2,4-diamine;
$N^4$-ethyl-$N^2$-(3-methyl-1-(2-(5-methyl-1,3,4-oxadiazol-2-yl)propan-2-yl)-1H-pyrazol-4-yl)-5-(trifluoromethyl)pyrimidine-2,4-diamine;
N4-ethyl-N2-(1-(2-(5-ethyl-1,3,4-oxadiazol-2-yl)propan-2-yl)-3-methyl-1H-pyrazol-4-yl)-5-(trifluoromethyl)pyrimidine-2,4-diamine;

N4-ethyl-N2-(1-(2-(1-isopropyl-1H-1,2,4-triazol-3-yl)propan-2-yl)-3-methyl-1H-pyrazol-4-yl)-5-(trifluoromethyl)pyrimidine-2,4-diamine;
N2-(3-chloro-1-(2-(4-methyl-4H-1,2,4-triazol-3-yl)propan-2-yl)-1H-pyrazol-4-yl)-N4-ethyl-5-(trifluoromethyl)pyrimidine-2,4-diamine;
N2-(3-chloro-1-(2-(1-methyl-1H-1,2,4-triazol-3-yl)propan-2-yl)-1H-pyrazol-4-yl)-N4-ethyl-5-(trifluoromethyl)pyrimidine-2,4-diamine;
N4-methyl-N2-(5-methyl-1-(2-(1-methyl-1H-pyrazol-3-yl)ethyl)-1H-pyrazol-4-yl)-5-(trifluoromethyl)pyrimidine-2,4-diamine;
N4-ethyl-N2-(3-methyl-1-(2-(1-methyl-1H-pyrazol-3-yl)propan-2-yl)-1H-pyrazol-4-yl)-5-(trifluoromethyl)pyrimidine-2,4-diamine;
N4-ethyl-N2-(3-methyl-1-(2-(1-methyl-1H-pyrazol-5-yl)propan-2-yl)-1H-pyrazol-4-yl)-5-(trifluoromethyl)pyrimidine-2,4-diamine;
N4-methyl-N2-(3-methyl-1-(2-(1-methyl-1H-pyrazol-3-yl)ethyl)-1H-pyrazol-4-yl)-5-(trifluoromethyl)pyrimidine-2,4-diamine;
N2-(1-(3-fluorotetrahydro-2H-pyran-4-yl)-3-methyl-1H-pyrazol-4-yl)-N4-methyl-5-(trifluoromethyl)pyrimidine-2,4-diamine;
N2-(1-(3-fluorotetrahydro-2H-pyran-4-yl)-3-methyl-1H-pyrazol-4-yl)-N4-methyl-5-(trifluoromethyl)pyrimidine-2,4-diamine;
N2-(1-(3-fluorotetrahydro-2H-pyran-4-yl)-5-methyl-1H-pyrazol-4-yl)-N4-methyl-5-(trifluoromethyl)pyrimidine-2,4-diamine;
N2-(1-((3R)-3-fluorotetrahydro-2H-pyran-4-yl)-5-methyl-1H-pyrazol-4-yl)-N4-methyl-5-(trifluoromethyl)pyrimidine-2,4-diamine
3-methyl-3-(3-methyl-4-((4-(methylamino)-5-(trifluoromethyl)pyrimidin-2-yl)amino)-1H-pyrazol-1-yl)butanenitrile;
2-((3-methyl-4-((4-(methylamino)-5-(trifluoromethyl)pyrimidin-2-yl)amino)-1H-pyrazol-1-yl)methyl)butanenitrile;
3-methyl-3-(3-methyl-4-(4-(methylamino)-5-(trifluoromethyl)pyrimidin-2-ylamino)-1H-pyrazol-1-yl)butanenitrile;
2-(5-((4-(ethylamino)-5-(trifluoromethyl)pyrimidin-2-yl)amino)-1-methyl-1H-pyrazol-3-yl)-2-methylpropanenitrile;
2-methyl-2-(1-methyl-5-((4-(methylamino)-5-(trifluoromethyl)pyrimidin-2-yl)amino)-1H-pyrazol-3-yl)propanenitrile;
2-((1-(2-cyanopropan-2-yl)-3-methyl-1H-pyrazol-4-yl)amino)-4-(cyclopropylamino)pyrimidine-5-carbonitrile;
2-((1-(2-cyanopropan-2-yl)-3-methyl-1H-pyrazol-4-yl)amino)-4-(cyclopropylamino)pyrimidine-5-carbonitrile;
2-((1-(2-cyanopropan-2-yl)-3-methyl-1H-pyrazol-4-yl)amino)-4-(ethylamino)pyrimidine-5-carbonitrile;
2-methyl-2-(3-methyl-4-((4-(methylamino)-5-(trifluoromethyl)pyrimidin-2-yl)amino)-1H-pyrazol-1-yl)butanenitrile; and
5-((4-(ethylamino)-5-(trifluoromethyl)pyrimidin-2-yl)amino)-1-methyl-1H-pyrazole-3-carbonitrile,
or a pharmaceutical salt thereof.

2. A composition comprising:
(a) a pharmaceutically acceptable carrier; and
(b) a compound of claim 1.

3. A method for treating Parkinson's disease, said method comprising administering to a subject in need thereof an effective amount of a compound of claim 1.

* * * * *